(12) United States Patent
Crooks et al.

(10) Patent No.: US 7,214,710 B2
(45) Date of Patent: *May 8, 2007

(54) PERMEABLE, WATER SOLUBLE, NON-IRRITATING PRODRUGS OF CHEMOTHERAPEUTIC AGENTS WITH OXAALKANOIC ACIDS

(75) Inventors: Peter A. Crooks, Lexington, KY (US); Tadeusz Cynkowski, Lexington, KY (US); Grazyna Cynkowska, Lexington, KY (US); Hong Guo, Belmont, MA (US); Paul Ashton, Watertown, MA (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/851,096

(22) Filed: May 24, 2004

(65) Prior Publication Data

US 2004/0214784 A1   Oct. 28, 2004

Related U.S. Application Data

(62) Division of application No. 09/565,079, filed on May 4, 2000, now Pat. No. 6,765,019.

(60) Provisional application No. 60/132,803, filed on May 6, 1999.

(51) Int. Cl.
*A61K 31/215* (2006.01)

(52) U.S. Cl. ............... 514/529; 514/506; 546/48; 546/301; 536/26

(58) Field of Classification Search ......... 514/529, 514/506; 546/48, 71, 301; 536/26
See application file for complete search history.

(56) References Cited

U.S. PATENT DOCUMENTS

| | | | |
|---|---|---|---|
| 4,009,283 A | 2/1977 | Herr et al. | |
| 4,053,638 A | 10/1977 | Litchfield et al. | |
| 4,083,974 A | 4/1978 | Turi | |
| 4,206,220 A | 6/1980 | Sloan | |
| 4,412,994 A | 11/1983 | Sloan | |
| 4,439,451 A | 3/1984 | Coleman | |
| 4,443,476 A | 4/1984 | Lomen | |
| 4,473,584 A | 9/1984 | Heckler | |
| 4,477,468 A | 10/1984 | Heckler | |
| 4,489,080 A | 12/1984 | Lomen | |
| 4,613,505 A | 9/1986 | Mizushima et al. | |
| 4,767,751 A | 8/1988 | Davis | |
| 4,786,495 A | 11/1988 | Bird et al. | |
| 4,897,417 A | 1/1990 | Patil et al. | |
| 4,935,508 A | 6/1990 | Kamachi et al. | |
| 4,937,253 A | 6/1990 | Gleason et al. | |
| 4,990,499 A | 2/1991 | Gupta et al. | |
| 5,196,438 A | 3/1993 | Martin et al. | |
| 5,482,965 A | 1/1996 | Rajadhyaksha | |
| 5,501,863 A | 3/1996 | Rossling et al. | |
| 5,578,637 A | 11/1996 | Lai et al. | |
| 5,614,549 A | 3/1997 | Greenwald et al. | |
| 5,650,510 A | 7/1997 | Webb, II et al. | |
| 5,654,466 A | 8/1997 | Stuk et al. | |
| 5,681,964 A | 10/1997 | Ashton et al. | |
| 5,707,984 A | 1/1998 | Tjoeng et al. | |
| 5,712,400 A | 1/1998 | Leanna et al. | |
| 5,714,148 A | 2/1998 | Burke et al. | |
| 5,847,003 A * | 12/1998 | Ptchelintsev et al. | 514/532 |
| 5,880,131 A | 3/1999 | Greenwald et al. | |
| 5,918,568 A | 7/1999 | Gjerlov | |
| 6,110,908 A | 8/2000 | Guthery | |

FOREIGN PATENT DOCUMENTS

| | | |
|---|---|---|
| CA | 1 148 165 | 3/1981 |
| EP | 0 357 495 | 3/1990 |
| EP | 0 494 370 B1 | 11/1991 |
| EP | 0 540 751 A1 | 5/1992 |
| WO | WO96/22303 | 1/1996 |
| WO | WO00/77020 A1 | 6/2000 |

OTHER PUBLICATIONS

Cynkowski et al.—Novel prodrug ester forms of hydroxyl-containing drugs. Mono- and dicarboxylic oxa acids conjugates—Book of Abstracts, 211th ACS National Meeting, New Orleans, LA, Mar. 24-28 1996, MEDI-029 Publisher: American Chemical Society.

Monkhouse et al.—Transdermal Drug Delivery—Problems and Promises 0 Drug Development and Industrial Pharmacy, 14(2&3), 1983-209 (1988).

Stoughton et al.—Azone® : A New Non-toxic Enhancer of Cutaneous Penetration -Drug Development and Industrial Pharmacy, ((4), 723-744 (1983).

Wells et al.—Mutagenicity and Cytotoxicity of N-Methyl-2-pyrrolidinone and 4-(Methylamino)butanoic Acid in *Salmonella*/Microsome Assay—Journal of Applied Toxicology, vol. 8(2), 135-139 (1988).

Akhter et al.—Absorption through human skin of ibuprofen an dflubiprofen; effect of doese variation, deposited drug films, occlusion and the penetration enhancer N-methyl-2-pyrrolidone—J. Pharm. Pharmacol. 1985, 37: 27-37.

Hoelgaard, et al.—Vehicle effect on topical drug delivery IV. Effect of N-methylpyrrolidone and polar lips on percutaneous drug transport—International Journal of Pharmaceutics, 43 (1988) 233-240.

Bennett, et al.—Optimization of bioavailiability of topical steriods: non-occluded penetration enhancers under thermodynamic control—J. Pharm. Pharmacol. 1985, 37: 298-304.

(Continued)

*Primary Examiner*—David Lukton
(74) *Attorney, Agent, or Firm*—McDermott Will & Emery LLP

(57) ABSTRACT

The present invention relates to the field of prodrugs of chemotherapeutic agents and method of use thereof.

2 Claims, 23 Drawing Sheets

OTHER PUBLICATIONS

Sasaki et al.—Enhancing effect of pyrrolidone derivatives on transdermal drug delivery. I.—International Journal of Pharmaceutics, 44 (1988) 15-24.

Cynkowski et al.—Novel prodrug ester forms of hydroxyl-containg drugs. Mono- and dicarboxylic oxa acids conjugates—Book of Abstracts, 211th ACS National Meeting, New Orleans, Mar. 24-28 1996, MEDI-029 Publisher: American Chemical Society.

Flynn—Mechanism of Percutaneous Absorption from Physicochemical Evidence—University of Michigan College of Pharmacy, pp. 17-42.

Wells et al.—Disposition and Metabolism of Double-Labeled [$^3$H and $^{14}$C] N-Methyl-2-Pyrrolidinone in the Rat—vol. 16, No. 2, 1988 The American Society for Pharmacology and Experimental Therapeutics.

Barry, et al.—Optimization of Bioavailability of Topical Steroids: Penetration Enhancers Under Occlusion—vol. 82, No. 1, The Journal of Investigation Dermatology, 82:49-52, 1984.

Sugibayashi, et al.—Effect of Several Penetration Enhancers on the Percutaneous Absorption of Indomethacin in Hairless Rats—Chem. Pharm. Bull. 36(4)1519-1528 (1988).

Chromey et al.—Toxicity of N-Methyl-2-pyrrolidone (NMP): Teratogenic, subchronic and Two-Year Inhalation Studies—Fundamental and Applied Toxicology 9, 222-235 (1987).

Cynkowska et al.—Structure-stability study of novel anti-HIV prodrugs of zalcitabine with acids, oxa acids and aminooxa acid derivatives—Book of Abstracts, 217th ACS National Meeting, Anaheim, Calif., Mar. 21-25, 1999, MEDI-170 Publisher: American Chemical Society.

Cynkowski, et al.—Synthesis and properties of novel codrugs of protease inhibitors with reverse transcriptase inhibitors—Book of Abstracts, 217th ACS National Meeting, Anaheim, CA, Mar. 21-25, 1999, MEDI-171, Publisher—American Chemical Society.

Cynkowska, et al.—Synthesis and propertis of biolabile prodrugs of zidovudine with polyoxa acids and short chain polyethylene glycols—Abstracts of Papers American Chemical Society, (1998) Vo. 215, No. 1-2, pp. MEDI 36.

Cynkowska, et al.—Synthesis and properties of biolabile prodrugs of didanosine with polyoxa acids, amino acids and short chain polyethylene glycols—Book of Abstracts, 216th ACS National Meeting, Boston, Aug. 23-27, 1998, MEDI-347 Publisher: American Chemical Society.

Greenwald, et al.—Camptothecin-20-PEG ester transport forms: the effect of spacer groups on antitumor activity—Bioorg. Med. Chem *1998), 6(5), 551-562.

* cited by examiner

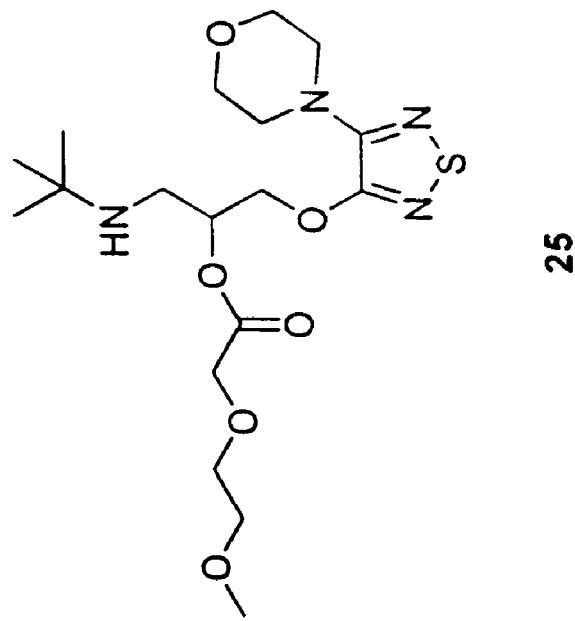
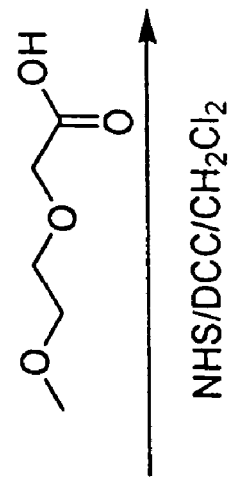
Figure 5
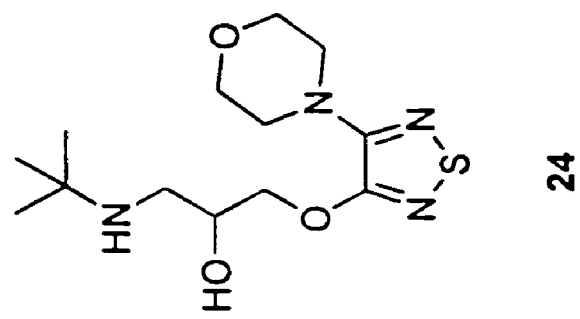

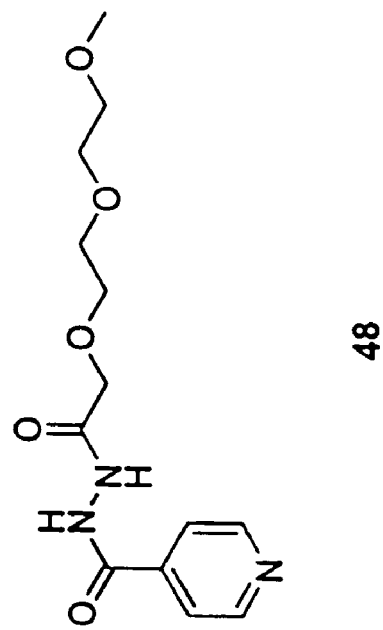
Figure 13
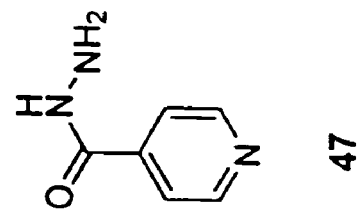

PERMEABLE, WATER SOLUBLE, NON-IRRITATING PRODRUGS OF CHEMOTHERAPEUTIC AGENTS WITH OXAALKANOIC ACIDS

This application is a divisional of application Ser. No. 09/565,079, filed May 4, 2000, now U.S. Pat. No. 6,765,019, which claims benefit of application 60/132,803, filed May 6, 1999.

FIELD OF THE INVENTION

The present invention relates to the field of prodrugs of chemotherapeutic agents and method of use thereof.

BACKGROUND OF THE INVENTION

U.S. Pat. No. 4,786,495 to Bird discloses flurbiprofen and salts thereof in admixture with an excipient encompassing fatty acid esters such as polyol esters of polyethylene glycol.

U.S. Pat. No. 5,681,964 to Ashton relates to soluble ester prodrugs of polyethylene glycol and various chemotherapeutic agents.

U.S. Pat. No. 4,767,751 to David discloses polyethylene glycol type solubilizers for flurbiprofen U.S. Pat. No. 4,613,505 to Mizushima discloses esters of flurbiprofen which may be dissolved in a vegetable oil and emulsified.

U.S. Pat. Nos. 4,489,080 and 4,443,476 to Lomen discloses alkyl esters of flurbiprofen.

U.S. Pat. No. 4,477,468 to Heckler discloses the systemic administration and topical application of flurbiprofen, salts thereof and esters thereof. The esters are ($C_1$–$C_8$) alkyl esters and are prescribed for the prophylactic and therapeutic treatment of herpes type II virus. U.S. Pat. Nos. 4,473,584, 4,443,476 and 4,439,451 are related to U.S. Pat. No. 4,477,468.

U.S. Pat. No. 4,412,994 to Sloan discloses hydroxamic derivatives of flurbiprofen as prodrugs U.S. Pat. No. 4,206,220 relates to compounds that are similar to those of U.S. Pat. No. 4,412,994. These compounds are aminoxy derivatives of, e.g., flurbiprofen.

U.S. Pat. No. 4,009,283 to Herr et al discloses lower alkyl esters of flurbiprofen. The esters are lower alkyl esters.

Canadian Patent CA 1,148,165 and German Patent DE 3,811,118 disclose esters of flurbiprofen.

The anti-inflammatory agent, flurbiprofen, produces local irritation when applied for treatment of inflammation. Various techniques have been used to lower the dosage of flurbiprofen to the patient, such as techniques for rapid release of flurbiprofen into the body. Nevertheless, there exists a need in the art for compositions that achieve the desired effects of flurbiprofen without the concomittant local irritation. This is particularly true in the application of the flurbiprofen anti-inflammatory agent to the eye.

DISCLOSURE OF THE INVENTION

An advantage of the present invention is to provide covalent conjugates of chemotherapeutic agents with mono- di- and polyoxaalkanoic or thiaalkanoic acids.

A further advantage of the present invention is the ability to adjust the solubility of steroidal molecules, lipophilicity and their half-life in the body and thus, bioavailability, by altering the structure and length of the oxaalkanoic acid or polyoxaalkanoic acid chain.

A further advantage of the present invention is to provide compounds having a chemotherapeutic effect which avoids or reduces the local irritation brought about by administration of the parent drug.

Another advantage of the present invention is to provide a pharmaceutical composition comprising a compound having a chemotherapeutic effect, but a reduced local irritation as compared to that produced by the parent drug.

Yet another advantage of the present invention is the ability of the prodrugs to permeate biological membranes, for example, the stratum corneum, and remain there until enzymatically cleaved, can be enhanced.

Additional advantages of the present invention will be set forth in the description which follows and in part will become apparent to those having ordinary skill in the art upon examination of the following or may be learned from the practice of the present invention. The objects and advantages of the invention may be realized and obtained as particularly pointed out in the appended claims.

According to the present invention, the foregoing and other advantages are achieved in part by providing a prodrug composition comprising a chemotherapeutic agent linked to a variety of oxaalkanoic acids of the formulas shown in Structures 1 and 2 wherein n=1–12. In a preferred embodiment n=1–6.

Additional advantages of the present invention will become readily apparent to those skilled in this art from the following detailed description, wherein embodiments of the present invention are described simply by way of illustrating of the best mode contemplated in carrying out the present invention. As will be realized, the present invention is capable of other and different embodiments, and its several details are capable of modifications in various obvious respects, all without departing from the present invention. Accordingly, the drawings and description are to be regarded as illustrative in nature and not as restrictive.

BRIEF DESCRIPTION OF DRAWINGS

FIGS. 1–23 illustrate sequential steps in synthesizing prodrugs according to various embodiments of the present invention.

FIG. 1 illustrates the steps for synthesis of prodrugs of triamcinolone acetonide.

FIG. 2 illustrates the steps for synthesis of prodrugs of camptothecin.

FIG. 3 illustrates the steps for synthesis of prodrugs of 5-fluorouracil.

FIG. 4 illustrates the steps for synthesis of prodrugs of ganciclovir.

FIG. 5 illustrates the steps for synthesis of a prodrug of timolol.

FIG. 6 illustrates the steps for synthesis of prodrugs of DDI.

FIG. 7 illustrates the steps for synthesis of dideoxycytidine (DDC)

FIG. 8 illustrates the steps for synthesis of prodrugs of DDC.

FIG. 9 illustrates the steps for synthesis of prodrugs of zidovudine.

FIGS. 10 and 11 illustrate the steps for synthesis of prodrugs of saquinavir.

FIG. 12 illustrates the steps for synthesis of prodrugs of ritonavir.

FIG. 13 illustrates the steps for synthesis of a prodrug of isoniazid.

FIG. 14 illustrates the steps for synthesis of ganciclovir.

FIG. 15 illustrates the steps for synthesis of combretastatin.

FIG. 16 illustrates the steps for synthesis of 2',3'-didehydrodideoxythymidine.

FIG. 17 illustrates the steps for synthesis of 2',3'-didehydrodideoxythymidine.

FIG. 18 illustrates the steps for synthesis of 3'-thiadideoxycytidine.

FIG. 19 illustrates the steps for synthesis of cyclosporin.

FIG. 20 illustrates the steps for synthesis of triamcinolone acetonide.

FIG. 21 illustrates the steps for synthesis of saquinavir.

FIG. 22 illustrates the steps for synthesis of saquinavir.

FIG. 23 illustrates the steps for synthesis of saquinavir.

DESCRIPTION OF THE INVENTION

Figure 1:
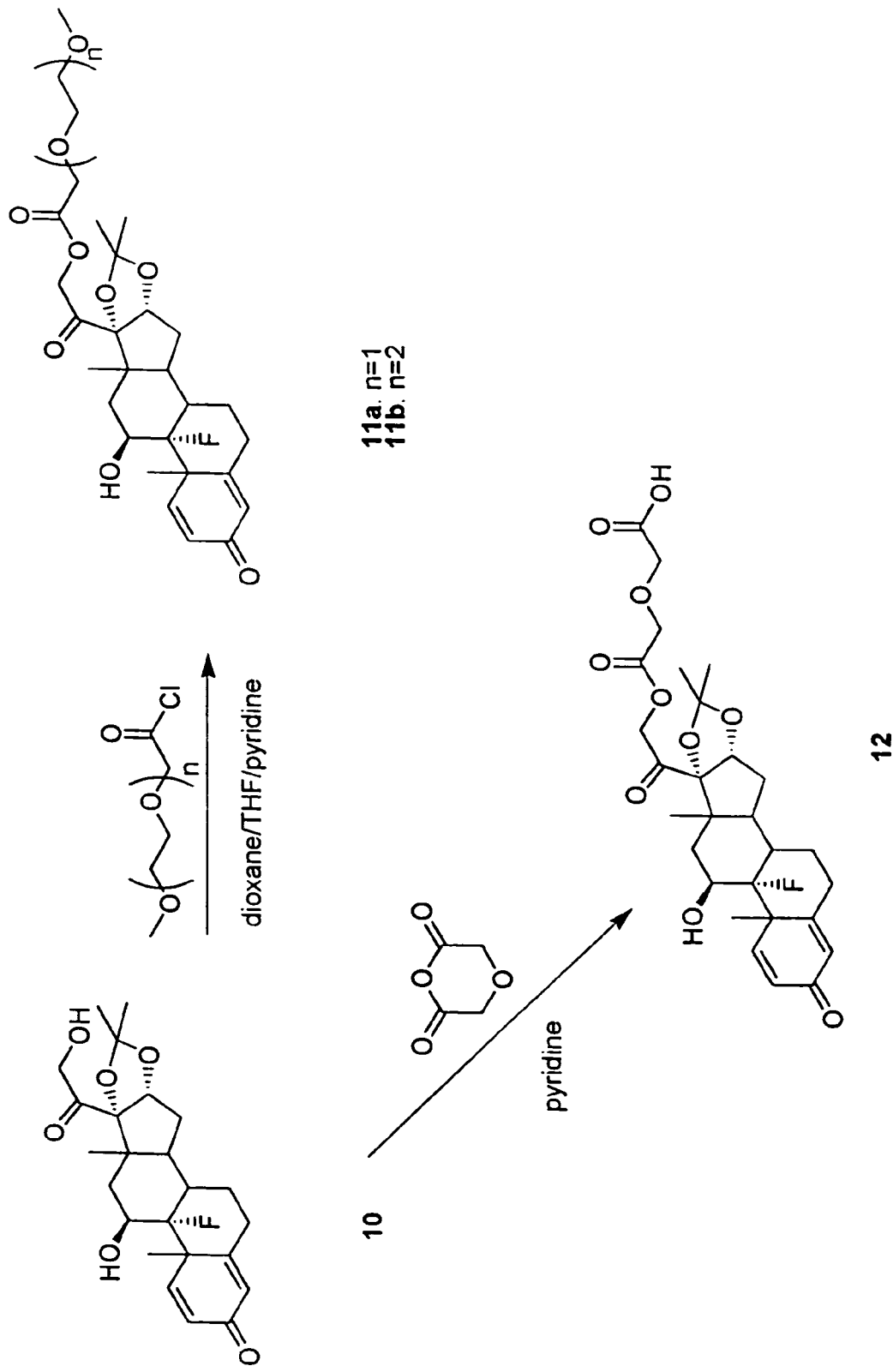

The present invention relates to soluble ester and amide prodrugs of various alkanoic acids, such as , oxaalkanoic acids, including thiaalkanoic acids, oxahydroxyalkanoic acids, oxaalkoxyalkanoic acids, oxadialkanoic acids, and oxaaminoalkanoic acids covalently linked to a chemotherapeutic agent.

Examples of chemotherapeutic agents, include, but are not limited to triamcinolone acetonide, AZT, DDI, DDC, acyclovir, ritonavir, saquinavir, gancyclovir, 5-fluorouracil, camptothecin, isoniazid, and timolol.

In accordance with this invention, provided are formulas 1 and 2 of the structural moieties that are covalently linked to the drug molecule to form the prodrug.

Formula 1 is

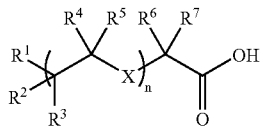

wherein X=0 or S; $R^1$=OH, $OR^8$ ($R^8$ is $C_1$–$C_4$ alkyl, $C_3$–$C_4$ branched alkyl, $C_3$–$C_4$ cycloalkyl), O—$CH_2$—COOH, $NHR^9$ ($R^9$ is H, $C_1$–$C_4$ alkyl, $C_3$–$C_4$ branched alkyl, $C_3$–$C_4$ cycloalkyl), $^+NH_2R^9Z^-$ ($Z^-$ is $Cl^-$, $Br^-$, $HSO_4^-$, $SO_4^{2-}$, $NO_3^-$, $HClO_4^-$, $I^-$, $H_2PO_4^{2-}$ $PO_4^{3-}$ and other pharmaceutically acceptable salt anions, including anions of pharmaceutically acceptable organic acids and organic diacids.

Pharmaceutically acceptable organic acids and organic diacids, include, for example, tartrate, maleate, fumarate, pivalate, mesylate, citrate, tosylate, ascorbate, mucate, acetate, benzoate, salicylate, and succinate.

$R^2$, $R^3$, $R^4$, $R^5$, $R^6$, and $R^7$ are selected from the group consisting of H, $C_1$–$C_4$ alkyl, $C_1$–$C_4$ hydroxyalkyl; and n is a number from 1 to 12.

Formula 2 is

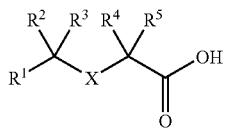

wherein X is O or S, $R^1$ is COOH, $CO_2R^6$($R^6$ is $C_1$–$C_4$ alkyl, $C_3$–$C_4$ branched alkyl, $C_3$–$C_4$ cycloalkyl); $R^2$, $R^3$, $R^4$, and $R^5$ are selected from a group consisting of H, $C_1$–$C_4$ alkyl, $C_1$–$C_4$ hydroxyalkyl.

Formulas 3 to 6 show the functionality on the drug molecule that is conjugated to alkanoic acid described in structures 1 and 2.

DRUG-C(=O)—OH     3

DRUG-X—H X=O or S     4

DRUG-NHR R=H or an N-substituent in the drug-molecule     5

DRUG-C(=O)—NHR R=H or an N-substituent in the drug molecule     6

The present invention provides drug conjugating moieties of the formula:

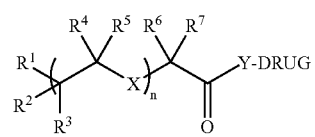

wherein Y is O, S, $NR^8$ ($R^8$ is H or $C_1$–$C_4$ alkyl, $C_3$–$C_4$ branched alkyl, or $C_3$–$C_4$ cycloalkyl); X is O or S; $R^1$ is OH, $OR^9$ ($R^9$ is $C_1$–$C_4$ alkyl, $C_3$–$C_4$ branched alkyl, and $C_3$–$C_4$ cycloalkyl), O—$CH_2$—COOH, $NH_2$ or $^+NH_3Z^-$ ($Z^-$ is $Cl^-$, $Br^-$, $HSO_4^-$, $SO_4^-$, $NO_3^-$, $HClO_4^-$, $I^-$, $H_2PO_4^-$, $HPO_4^-$, $HPO_4^{2-}$, $PO_4^{3-}$ and other pharmaceutically acceptable salt anions, including anions of pharmaceutically acceptable organic acids and diacids, including but not restricted to tartrate, maleate, pivalate, fumarate, mesylate, citrate, tosylate, ascorbate, mucate, acetate, benzoate, salicylate, and succinate); $R^2$ to $R^7$ are selected from the group consisting of H, $C_1$–$C_4$ alkyl, $C_1$–$C_4$ hydroxyalkyl; and n is a number from 1 to 12.

The present invention also provides drug conjugating moieties of the formula:

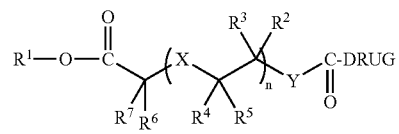

wherein Y is O, S, $NR^8$ ($R^8$ is H, or $C_1$–$C_4$ alkyl, $C_3$–$C_4$ branched alkyl, $C_3$–$C_4$ cycloalkyl); X is O or S; $R^1$ is H or $C_1$–$C_4$ alkyl, $C_3$–$C_4$ branched alkyl, or $C_3$–$C_4$ cycloalkyl; $R^2$ to $R^7$ are selected from the group consisting of H, $C_1$–$C_4$ alkyl, $C_1$–$C_4$ hydroxyalkyl; and n is a number from 1 to 12.

The present invention further provides drug conjugating moieties of the formula:

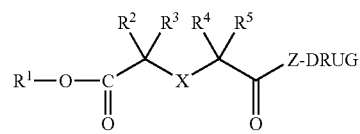

wherein X is O or S; Z is O, S, $NR^6$ ($R^6$ is H, $C_1$–$C_4$ alkyl, $C_3$–$C_4$ branched alkyl, $C_3$–$C_4$ cycloalkyl); $R^1$ is H, or $C_1$–$C_4$ alkyl, $C_3$–$C_4$ branched alkyl, or $C_3$–$C_4$ cycloalkyl; $R^2$ to $R^5$ are selected from the group consisting of H, $C_1$–$C_4$ alkyl, $C_1$–$C_4$ hydroxyalkyl.

The present invention includes alkali metal and alkali earth salts of drug conjugate 7, 8, and 9 when a free carboxylic acid moiety is present in the molecule.

Preferred compounds according to formula 7 are those wherein X=O, $R^1$ is OH, $OR^9$ ($R^9$=$C_1$–$C_4$ alkyl), $OCH_2COOH$, $NH_2$, and $R^2$, $R^3$, $R^4$, $R^5$, $R^6$, $R^7$ are hydrogen and n is a number from 1 to 6. Even more preferred are compounds according to formula 7 are those wherein $R^2$, $R^3$, $R^4$, $R^5$, $R^6$ and $R^7$ are hydrogen and n is 2, 4 or 6 and $R^1$ is OH, $OR^9$ ($R^9$=$CH_3$), $OCH_2COOH$.

Preferred compounds according to formula 8 are those wherein Y=O, $NR^8$ ($R^8$ is H or $C_1$–$C_4$ alkyl), X=0, and wherein R1 is H or $C_1$–$C_4$, and $R^2$, $R^3$, $R^4$, $R^5$, $R^6$, and $R^7$ are hydrogen, and n is 2, 4, or 6.

Preferred compounds according to formula 9 are those wherein X is O, Z is O or $NR^6$ ($R^6$ is H or $C_1$–$C_4$ alkyl), $R^1$ is H or $C_1$–$C_4$ alkyl, and $R^2$, $R^3$, $R^4$ and $R^5$ are H.

It should be appreciated that the compounds illustrated in formulas 7–9 may have one or more asymmetric carbon atoms and may exist as optical and/or diastereomeric isomers. For the purpose of this invention the racemic mixtures and dextro and levo forms, and all diastereomeric forms, are included within the present invention. The racemic mixtures are preferred.

Further, the compounds of the present invention are useful in pharmaceutical compositions for systemic administration to humans and animals in unit dosage forms, such as tablets, capsules, pills, powders, granules, suppositories, sterile parenteral solutions or suspensions, sterile non-parenteral solutions or suspensions oral solutions or suspensions, oil in water or water in oil emulsions and the like, containing suitable quantities of an active ingredient. Topical application can be in the form of ointments, creams, lotions, jellies, sprays, douches, and the like. For oral administration either solid or fluid unit dosage forms can be prepared with the compounds of Formulas 7–9. The compounds are useful in pharmaceutical compositions (wt %) of the active ingredient with a carrier or vehicle in the composition range 1–99%.

Either fluid or solid unit dosage forms can be readily prepared for oral administration. For example, the compounds of Formulas 7–9 can be mixed with conventional ingredients such as dicalcium phosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. Capsules may be formulated by mixing the compound with a pharmaceutical diluent which is inert and inserting this mixture into a hard gelatin capsule having the appropriate size. If soft capsules are desired a slurry of the compound with an acceptable vegetable, light petroleum, or other inert oil can be encapsulated by machine into a gelatin capsule.

Suspensions, syrups and elixirs may be used for oral administration of fluid unit dosage forms. A fluid preparation including oil may be used for oil soluble forms. A vegetable oil such as corn oil, peanut oil or safflower oil, for example, together with flavoring agents, sweeteners and any preservatives produces an acceptable fluid preparation. A surfactant may be added to water to form syrup for fluid unit dosages. Hydroalcoholic pharmaceutical preparations may be used having an acceptable sweetener such as sugar, saccharin or biological sweetener and a flavoring agent in the form of an elixir.

Pharmaceutical compositions for parenteral and suppository administration can also be obtained using techniques standard in the art.

Another use of the compounds according to the invention is as a topical agent, as appropriate, suitable for application to either the eyes, ears, or skin. Another additional use of the compounds is in a transdermal, parenteral pharmaceutical preparation, which in some examples may be particularly useful in the treatment of inflamed connective tissue in a mammal such as a human.

Accordingly, compositions suitable for administration to these areas are particularly included within the invention. The above parenteral solutions or suspensions may be administered transdermally and, if desired a more concentrated slow release form may be administered. Accordingly, incorporation of the active compounds in a slow release matrix may be implemented for administering transdermally. The compounds may be administered transdermally at about 1 to 20% of the composition and preferably about 5 to 15% wt % of the active ingredient in the vehicle or carrier.

Transdermal therapeutic systems are self-contained dosage forms that, when applied to intact skin, deliver drug(s) at a controlled rate to the systemic circulation. Advantages of using the transdermal routing include: enhanced therapeutic efficacy, reduction in the frequency of dosing, reduction of side effects due to optimization of the blood-concentration versus time profile, increased patient compliance due to elimination of multiple dosing schedules, bypassing the hepatic "first-pass" metabolism, avoiding gastrointestinal incompatibilities and providing a predicable and extended duration of activity. However, the main function of the skin is to act as a barrier to entering compounds. As a consequence, transdermal therapy has so far been restricted to a limited number of drugs that possess the desirable physicochemical properties for diffusion across the skin barrier. One effective method of overcoming the barrier function of the skin is to include a penetration enhancer in the formulation of a transdermal therapeutic system. See Barry, Brian W.: *Dermatological Formulations: Percutaneous Absorption* (Dekker, New York, 1983); Bronough et al, *Percutaneous Absorption, Mechanisms-Methodology-Drug Delivery*, (Marcel Dekker, New York, N.Y. 1985); and Monkhouse et al, Transdermal drug deliver-problems and promises. *Drug Dev. Ind. Pharm.,* 14, 183–209 (1988).

Thus, a penetration enhancer may also be included in the prodrug formulation, which may be of the type described below. Several different types of penetration enhancers have been reported such as dimethylsulfoxide, n-decyl methyl sulfoxide, N,N-dimethylacetamide, N,Ni-dimethylformamide, 1-dodecylazacycloheptan-2-one (Azone), propylene glycol, ethanol, pyrrolidones such as N-methyl-2-pyrrolidone (NMP) and surfactants. See Bronough et al, supra, and Stoughton et al, Azone: a New Non-toxic enhancer of percutaneous penetration. *Drug Dev. Inc. Pharm.,* 9, 725–744 (1983).

N-methyl-2-pyrrolidone is a versatile solvent which is miscible with water, ethyl alcohol, ether, chloroform, benzene, ethyl acetate and carbon disulfide. N-methyl-2-pyrrolidone has been widely used as a solvent in industrial processes such as petroleum refining, GAF Corp.: "M-Pyrol (N-methyl-2-pyrrolidone) Handbook.", GAF Corp., New York, 1972. It is currently used as a solubilizing agent in topical and parenteral veterinary pharmaceutical and is now under consideration for use in products intended for humans, Wells, D. A. et al: Disposition and Metabolism of Double-Labeled [$^3$H and $^{14}$C] N-methyl-2-pyrrolidone in the Rat. *Drug Met. Disps.,* 16, 243–249 (1988). Animal and human experiments have shown very little irritation or sensitization potential. Ames type assays and chronic exposure studies have not revealed any significant toxicity, Wells et al, Mutagenicity and Cytotoxicity of N-methyl-2-pyrrolidone and 4-(methyl amino) Butanoic Acid in the *Salmonella*/microsome Assay. *J. Appl. Tox.*, 8, 135–139 (1988). N-methyl-2-pyrrolidone has also been shown to be an effective penetration enhancer. Barry et al, Optimization an Bioavailability of Topical Steroids: Penetration Enhancers Under Occlusion. *J. Inv. Derm.*, 82, 49–52 (1984); Akter et al, Absorption Through Human Skin of Ibuprofen and Flurbiprofen; Effect of Dos Variation, Deposited Drug Films, Occlusion and Penetration Enhancer N-methyl-2-pyrrolidone. *J. Pharm. Pharmacol.*, 37, 27–37 (1984); Holegaard et al, Vesical Effect on Topical Drug Delivery IV. Effect of N-methyl-2-pyrrolidone and Polar Lipids on Percutaneous Transport. *Int. J. Pharm.*, 43, 233–240 (1988); Sugibayashi et al, Effect of Several Penetration Enhancers on the Percutaneous Absorption of Indomethacin in Hairless Rat. *Chem. Pharm. Bull.*, 36, 1519–1529 (1988); Bennett et al, Optimization of Bioavailability of Topical Steroids: Non-occluded Penetration Enhancers Under Thermodynamic Control. *J. Pharm. Pharmacol.*, 37, 298–304 (1985); Sasaki et al, Enhancing Effect of Pyrrolidone Derivatives on Transdermal Drug Delivery. 1. *Int. J. Pharm.*, 44, 14–24 (1988); Lee et al, Toxicity of N-methyl-2-pyrrolidone (NMP): Teratogenic, Subchronic and Two-year Inhalation Studies, *Fund. Appl., Tox.*, 9 222–235 (1987).

Compounds of formulas 7–9 can be present in the reservoir alone or in combination form with pharmaceutical carriers. The pharmaceutical carriers acceptable for the purpose of this invention are the art known carriers that do not adversely affect the drug, the host, or the material comprising the drug delivery device. Suitably pharmaceutical carriers include sterile water; saline, dextrose; dextrose in water or saline; condensation products of castor oil and ethylene oxide combining about 30 to 35 moles of ethylene oxide per mole of castor oil; liquid acid; lower alkanols; oils such as corn oil; peanut oil, sesame oil and the like, with emulsifiers such as mono- or di-glyceride of a fatty acid, or phosphatide, e.g., lecithin, and the like; glycols; polyalkylene glycols; aqueous media in the presence of a suspending agent, for example, sodium carboxymethylcellulose; sodium alginate; poly(vinylpyrrolidone); and the like, alone or with suitable dispensing agents such as lecithin; polyoxyethylene stearate; and the like. The carrier may also contain adjutants such as preserving, stabilizing, wetting, or emulsifying agents and the like together with the previously described penetration enhancers of this invention.

The effective dosage for mammals may vary due to such factors as age, weight activity level or condition of the subject being treated. Typically, an effective dosage of a compound according to the present invention is in the range 1 to 500 mg when administered by either oral or rectal dose from 1 to 3 time daily. This is about 0.02 to about 35 mg per kilogram of the subject's weight administered per day. Preferably about 5 to about 175 mg are administered orally or rectally 1 to 3 times a day for an adult human. The required dose is considerably less when administered parenterally, preferably about 1 to 15 mg may be administered intramuscularly or transdermally, 1 or 2 times a day for an adult human.

Compounds of the present invention may be administered topically at about 1 to 20% of the composition, and preferably about 5 to 15 wt %.

The compounds of the invention can be prepared by conventional esterification or acylation procedures known to those skilled in the art. For example, triamcinolone acetonide can be reacted with an appropriate oxaalkanoic acid chloride in the presence of base to produce the final product ester, according to the present invention.

The following non-limiting examples are given by way of illustration only.

EXAMPLES

Example 1

Prodrug from Camptothecin and 3,6,9-trioxadecanoic Acid [(Scheme 2)]

Figure 2:
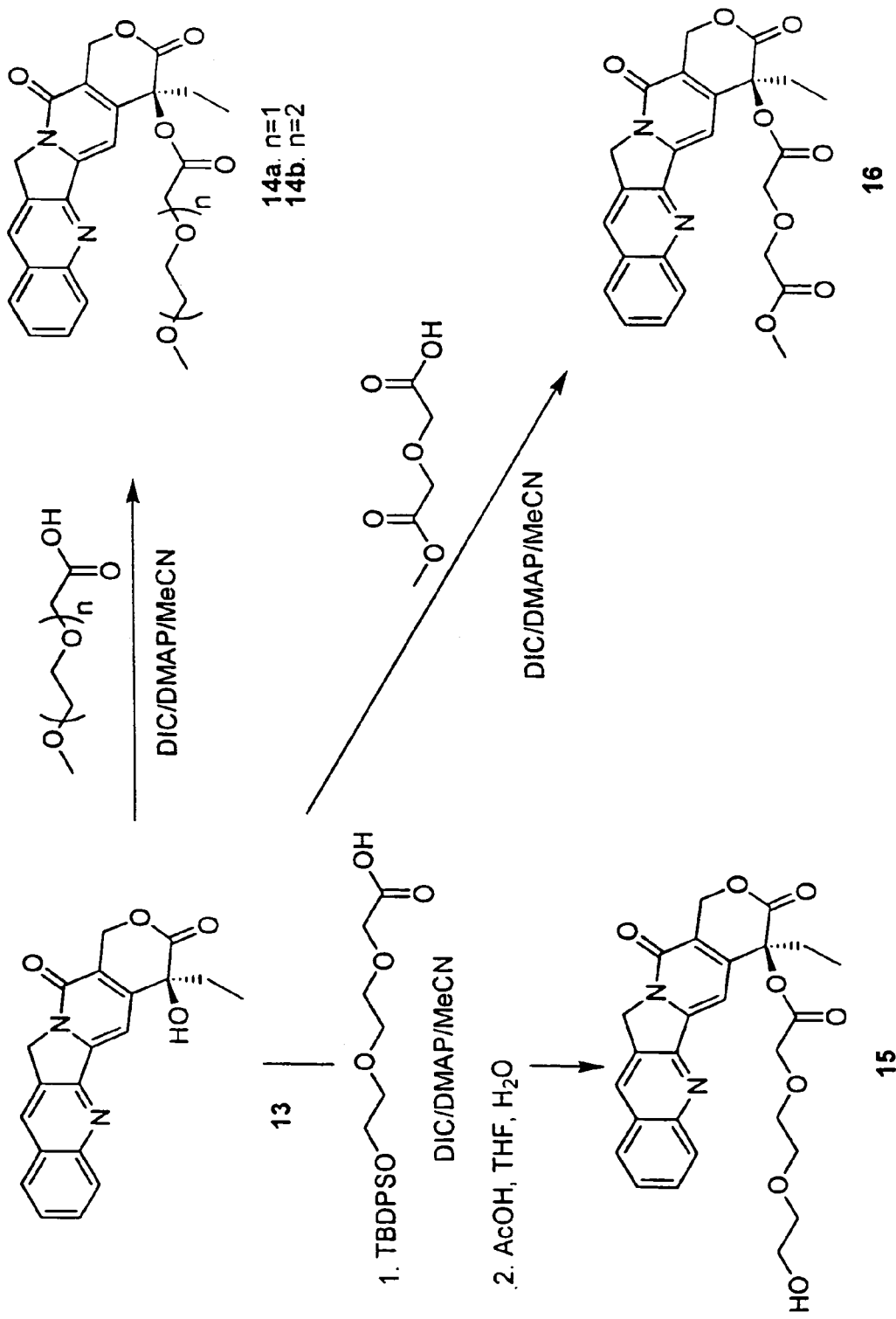

The reaction scheme is illustrated in FIG. 2. 40 mg of 3,6,9-trioxadecanoic acid was dissolved in 2.5 mL of anhydrous acetonitrile. To this stirred solution at room temperature was added 50 mg of camptothecin followed by 32 μL of diisopropylcarbodiimide and catalytical amount of DMAP. The resulting yellow suspension was stirred at room temperature overnight. The mixture was evaporated to dryness, the residue dissolved in 10 mL of chloroform, washed 3 times with water, once with brine and dried over sodium sulfate. Evaporation of the solvent left yellow solid, which was recrystallized from ethyl acetate/ether/hexane to afford 65 mg of the prodrug 14b. $^1$H NMR (CDCl$_3$) δ 0.98 (t, 3H, 19-CH$_3$), 2.22 (m, 2H, 18-CH$_2$), 3.36 (s, 3H, OCH$_3$), 3.50–3.80 (m, 8H, 4×OCH$_2$), 4.38 (s, 2H, OCH$_2$), 4 5.24 (s, 2H, 5-CH$_2$), 5.55 (dd, 2H, 17-CH$_2$), 7.22 (s, 1H, 14-CH), 7.66 (t, 1H), 7.82 (t, 1H), 7.92 (d, 1H), 8.21 (d, 1H), 8.40 (s, 1H, 7-CH).

Example 2

Prodrug of Camptothecin and 3,6-dioxaheptanoic Acid [(Scheme 2)]

The reaction scheme is illustrated in FIG. 2. 27 mg of 3,6-dioxaheptanoic acid was dissolved in 2 mL of anhydrous acetonitrile. To this stirred solution was added camptothecin (50 mg) and diisopropylcarbodiimide (32 μL) followed by 5 mg of DMAP. The resulting suspension was stirred at room temperature overnight, the evaporated and dissolved in chloroform (10 mL). The organic solution was washed with water (3 times), brine and dried over sodium sulfate. Evaporation of the extract left yellow solid residue which was recrystallized from ethyl acetate/ethyl ether to give 57 mg of pale yellow product 14b. $^1$H NMR (CDCl$_3$) δ 0.98 (t, 3H, 19-CH$_3$), 2.10–2.30 (m, 2H, 18-CH$_2$), 3.35 (s, 3H, OCH$_3$), 3.52 (m, 2H, OCH$_2$), 3.70 (m, 2H, OCH$_2$), 4.38 (d, 2H, OCH$_2$), 5.26 (s, 2H, 5-CH$_2$), 5.55 (dd, 2H, 17-CH$_2$), 7.20 (s, 2H, 14-CH), 7.65 (t, 1H), 7.82 (t, 1H), 7.92 (d, 1H), 8.20 (d, 1H), 8.40 (s, 1H, 7-CH).

Example 3

Prodrug of Camptothecin and Monomethyl Diglycolate [(Scheme 2)]

The reaction scheme is illustrated in FIG. 2. 50 mg of camptothecin and 32 mg of monomethyl ester of diglycolic acid were suspended in 2 mL of anhydrous acetonitrile. To this stirred mixture at room temperature was added 32 μL of diisopropylcarbodiimide followed by catalytical amount of DMAP. The resulting mixture was stirred at room temperature overnight, evaporated to dryness and redissolved in 10 mL of chloroform. The organic solution was washed 3 times with water, aqueous sodium bicarbonate and brine, followed by drying over sodium sulfate. The crude product after solvent evaporation was purified by preparative TLC in chloroform:methanol 35:1. The prodrug 16 was collected as a pale yellow solid (54 mg).

$^1$H NMR (CDCl$_3$) δ 1.00 (t, 3H, 19-CH$_3$), 2.20 (m, 2H, 18-CH$_2$), 3.74 (s, 3H, OCH$_3$), 4.26 (m, 2H, OCH$_2$), 4.45 (d, 2H, OCH$_2$), 5.26 (s, 2H, 5-CH$_2$), 5.56 (dd, 2H, 17-CH$_2$), 7.20 (s, 1H, 14-CH), 7.65 (t, 1H), 7.82 (t, 1H), 7.94 (d, 1H), 8.21 (d, 1H), 8.42 (s, 1H, 7-CH).

Example 4

Prodrug of Triamcinolone Acetonide and Diglycolic Acid [(Scheme 1)]

The reaction scheme is illustrated in FIG. 1. 50 mg of triamcinolone acetonide and 27 mg of diglycolic anhydride were dissolved in 1.5 mL of anhydrous pyridine under argon. The resulting solution was heated at 60° C. for 48 hours. The cooled mixture was diluted with cold 1M hydrochloric acid to form a colorless precipitation. The product was collected by filtration and washed with cold water until the washings were neutral to litmus paper. The prodrug was dried under high vacuum to afford 55 mg of 12. $^1$H NMR (CDCl$_3$) δ 0.92 (s, 3H, 18-CH$_3$), 1.21 (s, 3H, 19-CH$_3$), 1.42, 1.57 (2s, 6H, acetonide), 4.30 (s, 2H, OCH$_2$), 4.42 (s, 2H, OCH$_2$), 4.43 (m, 1H, 16-CH), 4.98 (m, 1H, 11-H), 5.02 (dd, 2H, 21-CH$_2$), 6.18 (s, 1H, 4-CH), 6.40 (d, 1H, 2-CH), 7.34 (d, 1H, 1-CH).

Example 5

Prodrug of Ganciclovir and 3,6,9-trioxadecanoic Acid [(Scheme 4)]

Figure 4:
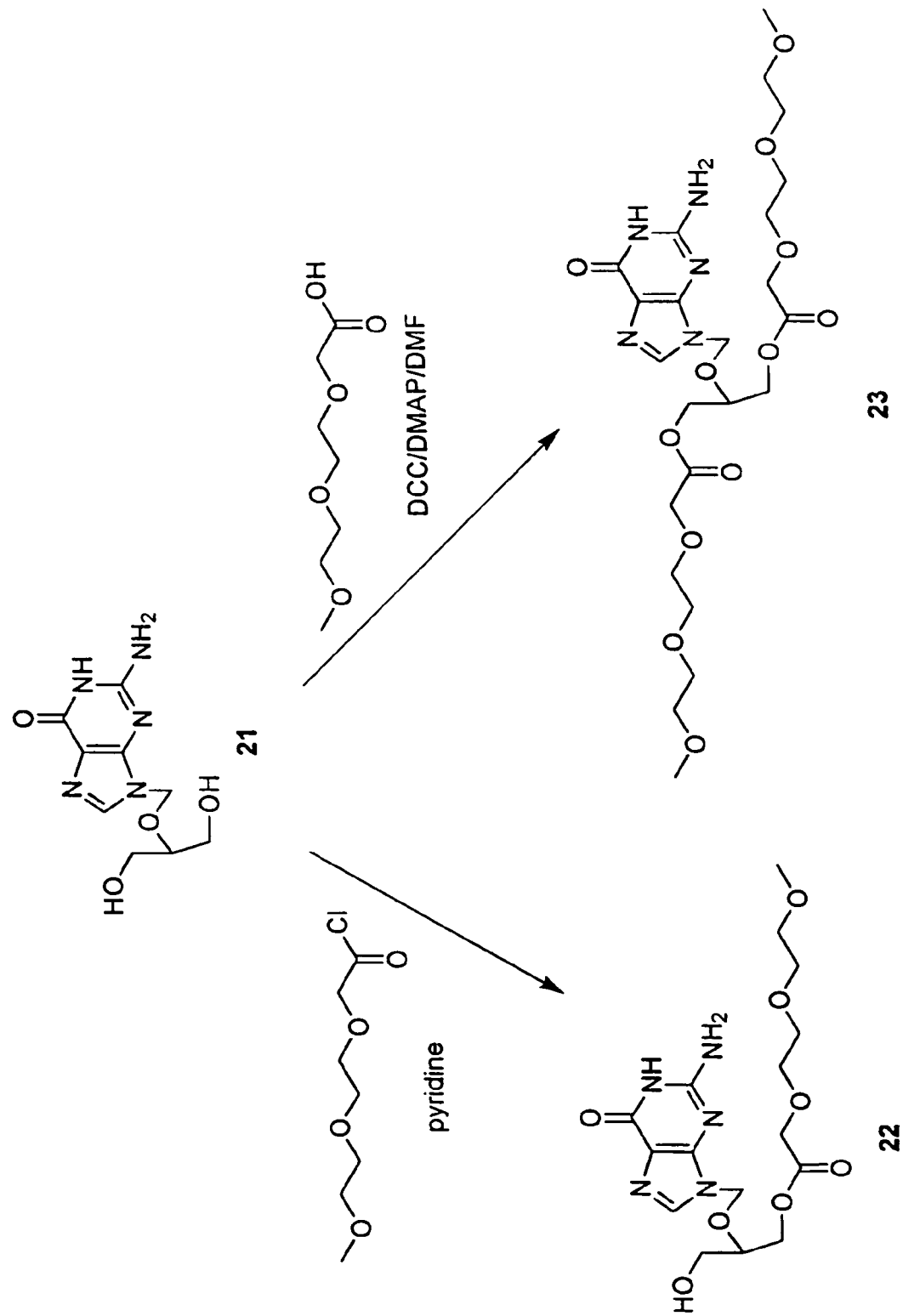

The reaction scheme is illustrated in FIG. 4. 140 mg of 3,6,9-trioxadecanoic acid was dissolved in 2 mL of anhydrous DMF at room temperature under argon. To this stirred solution was added 162 mg of dicyclohexylcarbodiimide followed by catalytical amount of DMAP. The resulting cloudy mixture was stirred at room temperature overnight. The solvent was removed in vacuo and the residue was dissolved in 30 mL of chloroform. The solution was washed with aqueous sodium bicarbonate, brine and dried over anhydrous sodium sulfate. Evaporation of the solvent left solid residue, which was purified by column chromatography on silica gel. Washing with chloroform-methanol, 15:1 yielded 80 mg of the pure prodrug 23. $^1$H NMR (CDCl$_3$) δ 3.38 (s, 6H, 2×OCH$_3$), 3.55–3.70 (m, 17H, 8×OCH$_2$, 4'-CH), 4.09 (s, 4H, 2×OCH$_2$), 5.50 (s, 2H, 1'CH$_2$), 6.20 (s, 2H, NH$_2$), 7.76 (s, 1H, 8-CH), 11.60 (s, 1H, NH).

Example 6

Prodrug of Triamcinolone Acetonide and 3,6,9-trioxadecanoic Acid [(Scheme 1)]

The reaction scheme is illustrated in FIG. 1. A solution of triamcinolone acetonide (100 mg) in dioxane (5 mL) and THF (2 mL) was cooled to 0° C. in an ice bath and pyridine (28 μL) was added followed by acid chloride prepared from 3,6-dioxaheptanoic acid (53 mg). The resulting homogenous solution was stirred at room temperature overnight and evaporated to dryness. The residue was dissolved in chloroform (20 mL), and the solution was washed with aqueous sodium bicarbonate, water and brine. The residue after drying the solvent evaporation was chromatographed on silica gel using chloroform-methanol, 75:1. The prodrug 11a was isolated as a colorless solid. Yield 90 mg. $^1$H NMR (CDCl$_3$) δ 0.95 (s, 3H, 18-CH$_3$), 1.21 (s, 3H, 19-CH$_3$), 1.43, 1.55 (2s, 6H, acetonide), 3.39 (s, 3H, OCH$_3$), 3.60, 3.76, (2m, 4H, 2×OCH$_2$), 4.31 (s, 2H, OCH$_2$), 4.42 (m, 1H, 11-CH), 4.98 (dd, 2H, 21-CH$_2$), 4.98 (m, 1H, OH), 6.13 (s, 1H, 4-CH), 6.35 (d, 1H, 2-CH), 7.24 (d, 1H, 1-CH).

Example 7

Prodrug of Triamcinolone Acetonide and 3,6,9-trioxadecanoic Acid [(Scheme 1)]

The reaction scheme is illustrated in FIG. 1. To a stirred solution of triamcinolone acetonide (160 mg) in dioxane (5 mL) and THF (2 mL) at 0° C. was added pyridine (45 μL) followed by acid chloride of 3,6,9-trioxadecanoic acid (108 mg). The resulting slightly cloudy mixture was stirred at room temperature overnight and the solvents were removed under vacuum. The residue was dissolved in chloroform (30 mL), washed with aqueous sodium bicarbonate (10 mL), water (10 mL) and brine (10 mL). The extract was dried over sodium sulfate and the solvent was evaporated. The oily residue was purified by column chromatography on silica gel using chloroform:methanol 70:1. The prodrug 11b (206 mg) was obtained as a white powder. $^1$H NMR (CDCl$_3$) δ 0.94 (s, 3H, 18-CH$_3$), 1.21 (s, 3H, 19-CH$_3$), 1.43, 1.55 (2s, 6H, acetonide), 3.38 (s, 3H, OCH$_3$), 3.57, 3.66, 3.71, 3.78 (4m, 8H, 4×OCH$_2$), 4.32 (s, 2H, OCH$_2$), 4.42 (m, 1H, 11-CH), 4.98 (dd, 2H, 21-CH$_2$), 4.98 (m, 1H, OH), 6.13 (s, 1H, 4-CH), 6.35 (d, 1H, 2-CH), 7.22 (d, 1H, 1-CH).

Example 8

Prodrugs of 5-fluorouracil with 3,6-dioxaheptanoic Acid [(Scheme 3)]

Figure 3:
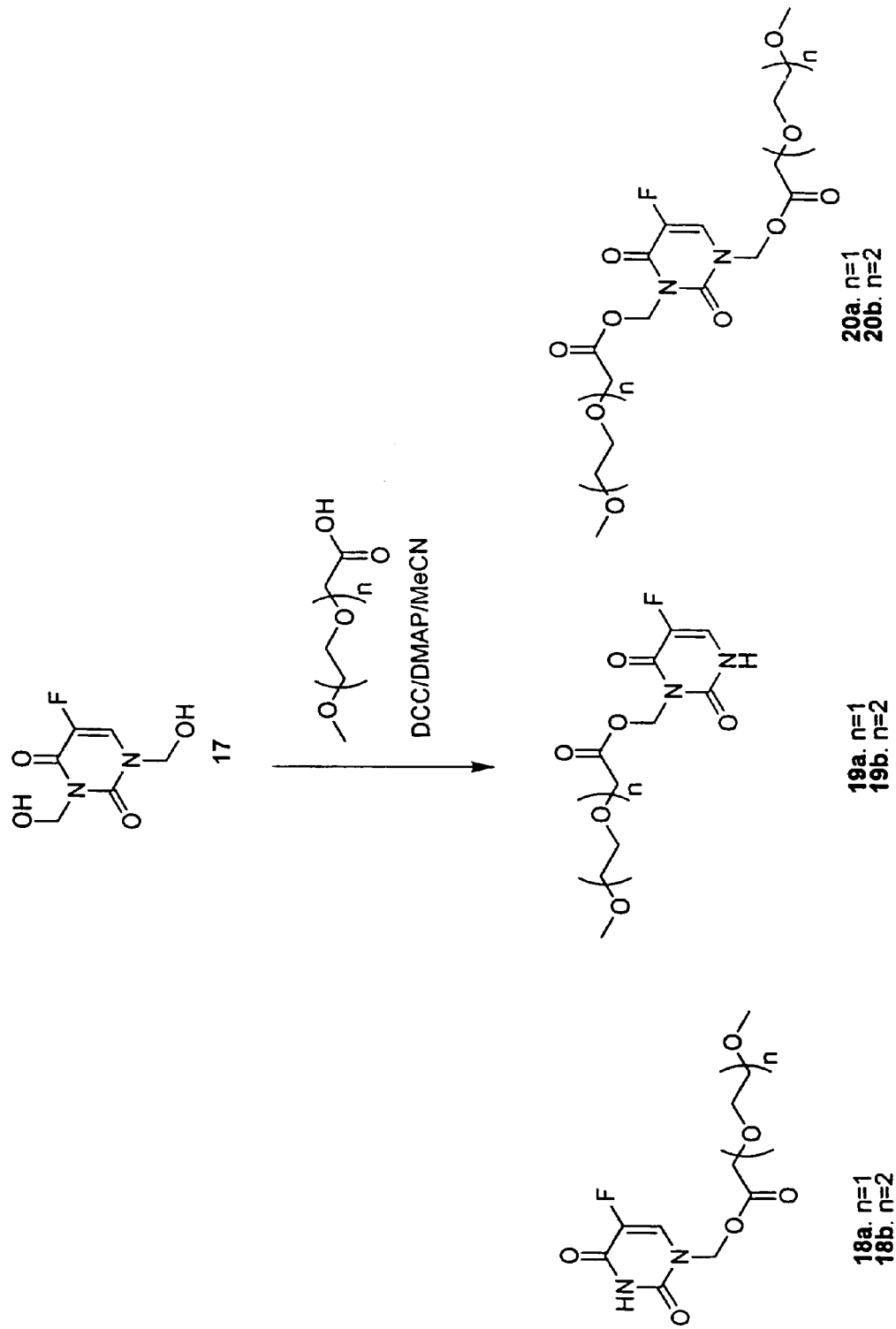

The reaction scheme is illustrated in FIG. 3. To a homogenous solution of crude 1,3-bis(hydroxymethyl)-4-fluorouracil (171 mg) and 3,6-dioxaheptanoic acid (145 mg) in anhydrous acetonitrile (3 mL) was added at room temperature dicyclohexylcarbodiimide (223 mg) followed by DMAP (10 mg). The mixture turned cloudy almost immediately and was stirred at room temperature overnight. After the reaction was complete, the solvents were removed under vacuum and the residue was treated with chloroform (25 mL). The suspension was filtered to remove byproducts and the filtrate was evaporated to yield crude mixture of products, which was purified by column chromatography on silica gel. Elution with chloroform:methanol 40:1 afforded three separate products: N1,N3-bissubstituted prodrug 20a (45 mg), N1 substituted prodrug 18a (120 mg) and N3 substitute prodrug 19a (12 mg) as colorless oils. $^1$H NMR (CDCl$_3$) δ of 20a, 3.79 (s, 6H, 2×OCH3), 3.58 (m, 4H, 2×OCH$_2$), 3.73 (m, 4H, 2×OCH$_2$), 4.18 (s, 2H, OCH$_2$), 4.25 (s, 2H, OCH$_2$), 5.74 (s, 2H, NCH$_2$), 6.04 (s, 2H, NCH$_2$), 7.71 (d, 1H, 6-CH). $^1$H NMR (CDCl$_3$) δ of 18a, 3.38 (s, 3H, OCH$_3$), 3.60 (m, 2H, OCH$_2$), 3.75 (m, 2H, OCH$_2$), 4.25 (s, 2H, OCH$_2$), 5.72 (s, 2H, NCH$_2$), 7.69 (d, 1H, 6-CH), 10.15 (d, 1H, NH). $^1$H NMR (CDCl$_3$) δ of 19a, 3.38 (s, 3H, OCH$_3$), 3.59 (m, 2H, OCH$_2$), 3.74 (m, 2H, OCH$_2$), 4.20 (s, 2H, OCH$_2$), 6.03 (s, 2H, NCH$_2$), 7.41 (d, 1H, 6-CH).

Example 9

Prodrugs of 5-fluorouracil and 3,6,9-trioxadecanoic Acid [(Scheme 3)]

The reaction scheme is illustrated in FIG. 3. To a stirred solution of crude 1,3-bis(hydroxymethyl)-5-fluorouracil (172 mg) in 3 mL of anhydrous acetonitrile at 0° C. was added 3,6,9-trioxadecanoic acid (193 mg) followed by dicyclohexylcarbodiimide (223 mg) and DMAP (10 mg). The reaction mixture turned cloudy almost immediately and was stirred at room temperature overnight. The solvent was evaporated to dryness and the residue was taken into chloroform (25 mL). The mixture was filtered to remove byproducts and the filtrate was evaporated. The residue was absorbed on silica gel and chromatographed with chloroform:methanol 25:1. Three products of the reaction were isolated as colorless oils; N1, N3-bissubstituted prodrug 20b (90 mg), N1-monosubstituted prodrug 18b (70 mg) and N3-monosubstituted prodrug 19b (23 mg). $^1$H NMR (CDCl$_3$) δ of 20b, 3.37 (s, 6H, 2×OCH3), 3.54, 3.63, 3.69, 3.75 (4m, 16H, 8×OCH$_2$), 4.18 (s, 2H, OCH$_2$), 4.26 (s, 2H, OCH$_2$), 5.74 (s, 2H, NCH$_2$), 6.03 (s, 2H, NCH$_2$), 7.75 (d, 1H, 6-CH). $^1$H NMR (CDCl$_3$) δ of 18b, 3.38 (s, 3H, OCH$_3$), 3.56, 3.64, 3.70, 3.75 (4m, 8H, 4×OCH$_2$), 4.25 (m, 2H, OCH$_2$), 5.71 (s, 2H, NCH$_2$), 7.68 (d, 1H, 6-CH), 9.96 (d, 1H, NH). $^1$H NMR (CDCl$_3$) δ of 19b, 3.38 (s, 3H, OCH$_3$), 3.57, 3.64, 3.70, 3.74 (4m, 8H, 4×OCH$_2$), 4.18 (s, 2H, OCH$_2$), 6.02 (s, 2H, NCH$_2$), 7.48 (d, 1H, 6-CH).

Example 10

Prodrug of Camptothecin and 8-hydroxy-3,6-dioxaoctanoic Acid [(Scheme 2)]

The reaction scheme is illustrated in FIG. 2. 50 mg of camptothecin and 58 mg of O-silylated 8-hydroxy-3,6-dioxaoctanoic acid were suspended in 2 mL of anhydrous acetonitrile at room temperature. To this stirred mixture at room temperature was added 32 μL of diisopropylcarbodiimide followed by catalytical amount of DMAP. The resulting yellow mixture was stirred at room temperature overnight, the solvent was evaporated under vacuum and the residue dissolved in chloroform. The solution was filtered, washed with aqueous sodium bicarbonate, twice with water, once with brine and dried over sodium sulfate. The residue after solvent evaporation was purified by column chromatography on silica gel using chloroform:methanol 80:1 to yield 60 mg of the oily ester. This intermediate product was dissolved in 2 mL of a mixture of acetic acid (3 parts), THF (1 part) and water (1 part). The resulting yellow homogenous solution was stirred at room temperature for 17 hours and then evaporated to dryness. The residue was dissolved in 10 mL of chloroform and washed with aqueous sodium bicarbonate, twice with water and once with brine. Drying over sodium sulfate following the solvent evaporation yielded 45 mg of crude product. The prodrug was purified by preparative TLC in chloroform-methanol, 30:1 to afford 40 mg of 15 as a pale yellow powder. $^1$H NMR (CDCl$_3$) δ 0.99 (t, 3H, 19-CH$_3$), 2.20 (m, 2H, 18-CH$_2$), 3.60–3.80 (m, 8H, 4×OCH$_2$), 4.40 (dd, 2H, OCH$_2$), 5.30 (s, 2H, 5-CH$_2$), 5.56 (dd, 2H, 17-CH$_2$), 7.28 (s, 1H, 14-CH), 7.68 (t, 1H), 7.85 (t, 1H), 7.96 (d, 1H), 8.22 (d, 1H), 8.42 (s, 1H, 7-CH).

Example 11

Monoester of Ganciclovir and 3,6,9-trioxadecanoic Acid [(Scheme 4)]

The reaction scheme is illustrated in FIG. 4. To a stirred suspension of ganciclovir (100 mg) in anhydrous pyridine (4 mL) was added at +10° C. acid chloride prepared from 3,6,9-trioxadecanoic acid. The mixture was stirred at room temperature overnight and then was evaporated to dryness. The crude solid residue was absorbed on silica gel and chromatographed with chloroform-methanol, 12:1. The monoesterified prodrug 22 was isolated as colorless oil (45 mg) $^1$H NMR (CD$_3$OD) δ 3.34 (s, 3H, OCH$_3$), 3.50–3.65 (m, 10H, 5×OCH$_2$), 3.96 (m, 1H, CH), 4.02 (s, 2H, OCH$_2$), 4.05–4.33 (m, 2H, OCH$_2$), 5.55 (dd, 2H, NCH$_2$), 7.84 (s, 1H, CH).

Example 12

Prodrug of DDI and 3,6,9-trioxadecanoic Acid [(Scheme 6)]

Figure 6:
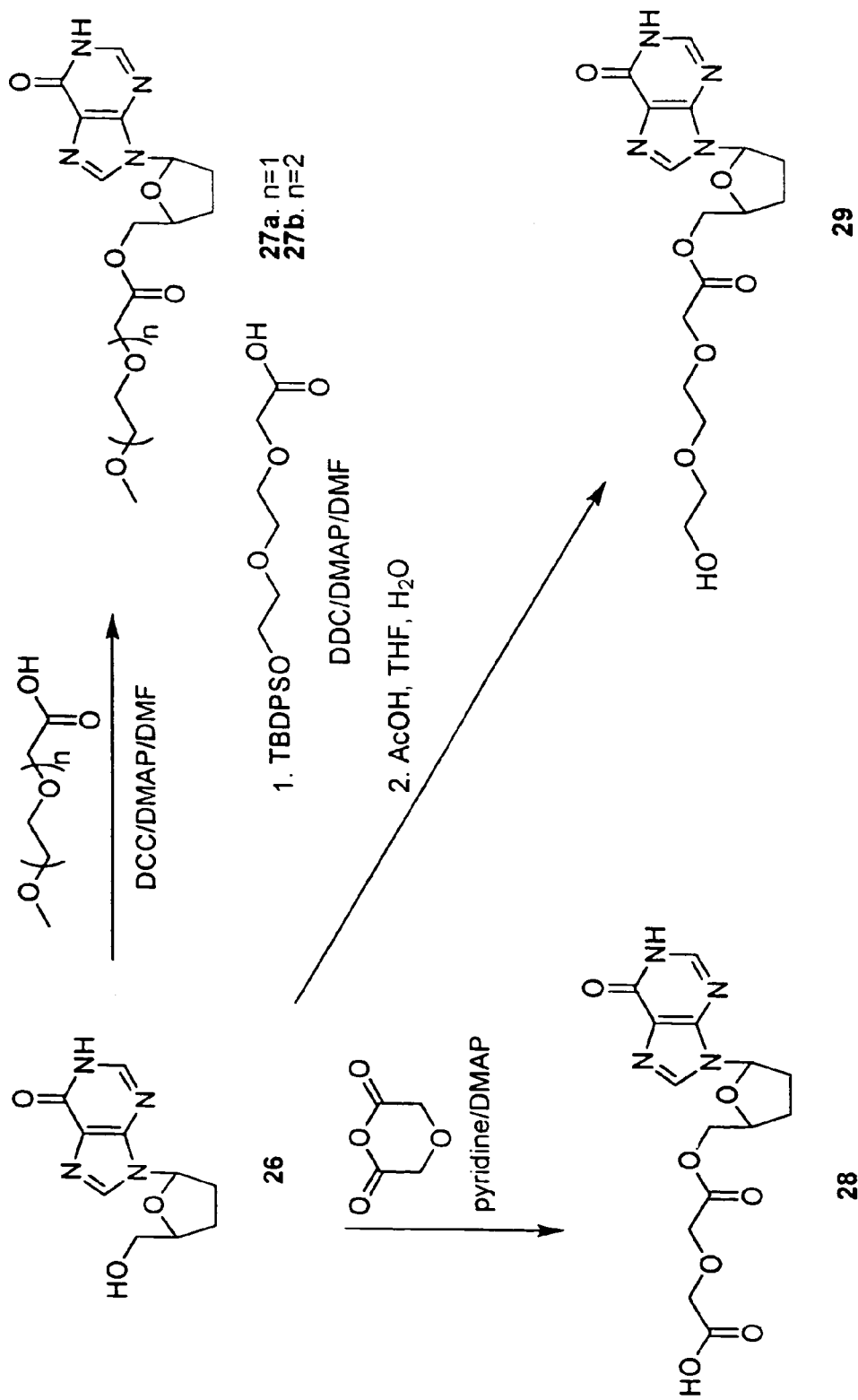
Figure 7:
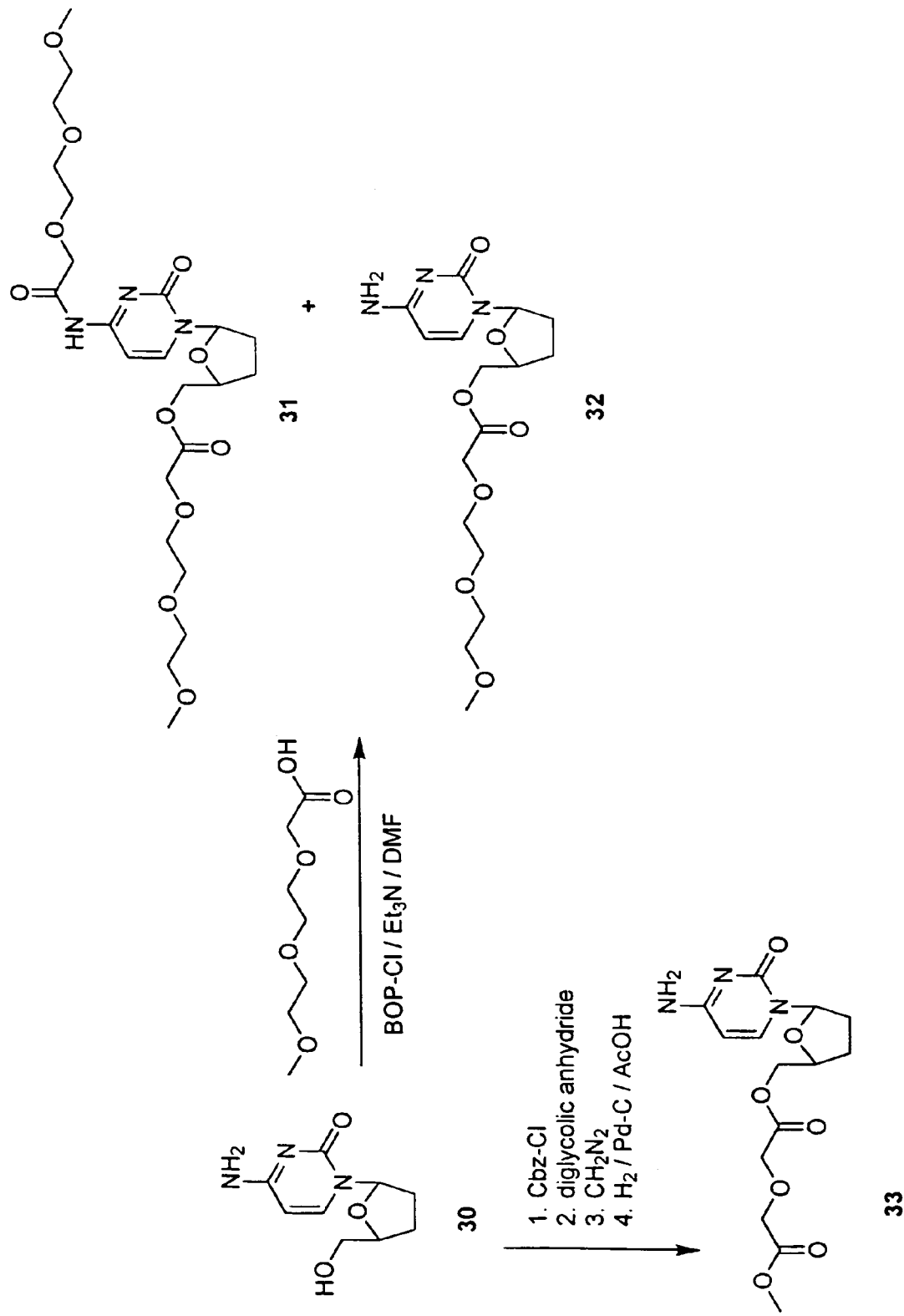

The reaction scheme is illustrated in FIG. 6. To a stirred solution of 3,6,9-trioxadecanoic acid (53 mg) in anhydrous DMF (2 mL) was added dicyclohexylcarbodiimide (61 mg) followed by DDI (50 mg) and catalytical amount of DMAP. The cloudy reaction mixture turned homogenous after a few minutes and was stirred at room temperature overnight. The resulting solution was evaporated to dryness under high vacuum, and the residue was dissolved in 40 mL of chloroform. The organic solution was washed with water (10 mL), aqueous sodium bicarbonate (10 mL) and brine (10 mL) before drying over sodium sulfate. The crude product after solvent evaporation was then purified by silica gel column chromatography (chloroform-methanol, 24:1) to give the pure prodrug 27b (37 mg) as a colorless oil. $^1$H NMR (CDCl$_3$) δ 2.14 (m, 2H, CH$_2$), 2.58 (m, 2H, CH$_2$), 3.36 (s, 3H, OCH$_3$), 3.50–3.80 (m, 8H, 4×OCH$_2$), 4.19 (s, 2H, OCH$_2$), 4.42 (m, 3H, 5'-CH$_2$, 4'-CH), 6.29 (t, 1H, 1'-CH), 8.12 (s, 1H, CH), 8.23 (s, 1H, CH), 12.95 (s, 1H, NH).

Example 13

Prodrug of DDI and 3,6-dioxaheptanoic Acid [(Scheme 6)]

The reaction scheme is illustrated in FIG. 6. To a stirred solution of 3,6-dioxaheptanoic acid (57 mg) in 2 mL of anhydrous acetonitrile at room temperature was added DMAP (5 mg) followed by dicyclohexylcarbodiimide (60 mg). The resulting solution was stirred for 15 min at room temperature and then the suspension of DDI (50 mg) in acetonitrile (2 mL) was added in one portion. The resulting cloudy mixture was stirred at room temperature for 48 hours. The solvent was removed under vacuum and the residue was dissolved in chloroform. The solution was washed with aqueous sodium bicarbonate, water, brine and dried over Na$_2$SO$_4$. The oily, colorless residue after solvent evaporation was purified by column chromatography on silica gel (chloroform-methanol, 25:1) to afford 41 mg of the pure prodrug 27a. $^1$H NMR (CDCl$_3$) δ 2.19 (m, 2H, CH$_2$), 2.58 (m, 2H, CH$_2$), 3.36 (s, 3H, OCH$_3$), 3.59 (m, 2H, OCH$_2$), 3.73 (m, 2H, OCH$_2$), 4.20 (s, 2H, OCH$_2$), 4.44 (m, 3H, 5'-CH$_2$, 4'-CH), 6.30 (t, 1H, 1'-CH), 8.13 (s, 1H, CH), 8.26 (s, 1H, CH), 13.20 (s, 1H, NH).

Example 14

Prodrug of DDI and 8-hydroxy-3,6-dioxaoctanoic Acid [(Scheme 6)]

The reaction scheme is illustrated in FIG. 6. To a stirred solution of DDI (50 mg) and silylated 8-hydroxy-3,6-dioxaoctanoic acid (122 mg) in anhydrous DMF (2 mL) was added at room temperature dicyclohexylcarbodiimide (87 mg) followed by DMAP (10 mg). The resulting cloudy mixture was stirred at room temperature overnight, then was filtered and evaporated to dryness. The crude residue was dissolved in chloroform (15 mL) and washed 0.5M HCl, aqueous sodium bicarbonate and xbrine. Drying over $Na_2SO_4$ followed by solvent evaporation left solid residue which was dissolved in 4 mL of a mixture of acetic acid (3 parts), THF (1 part) and water (1 part). The solution was stirred at room temperature until the reaction was complete (3 hours). The solution was evaporated to dryness and the crude product was purified by preparative TLC on silica gel plate in chloroform-methanol, 5:1. The prodrug 29 was isolated as colorless oil. Yield 37 mg. $^1H$ NMR ($CDCl_3$) δ 2.18 (m, 2H, $CH_2$), 2.60 (m, 2H, $CH_2$), 3.62 (m, 2H, $OCH_2$), 3.72 (m, 6H, 3×$OCH_2$), 4.20 (s, 2H, $OCH_2$), 4.44 (m, 3H, 5'-$CH_2$, 4'-CH), 6.29 (t, 1H, 1'-CH), 8.17 (s, 1H, CH), 8.24 (s, 1H, CH).

Example 15

Prodrug of DDI with Diglycolic Acid [(Scheme 6)]

The reaction scheme is illustrated in FIG. 6. DDI (100 mg) was evaporated with anhydrous pyridine (2.5 mL) at room temperature under high vacuum and then was suspended in 2.5 mL of anhydrous pyridine. To this stirred mixture at room temperature was added diglycolic anhydride (74 mg) followed by DMAP (52 mg). The resulting homogenous solution was stirred at room temperature overnight and then was poured into ice cold ethyl ether (25 mL). A precipitated solid product was collected by decantation and washed twice with cold ether and died under high vacuum. 133 mg of a colorless prodrug 28 was obtained. $^1H$ NMR (DMSO-$d_6$) δ 2.10 (m, 2H, $CH_2$), 3.90 (s, 2H, $OCH_2$), 4.06 (s, 2H, $OCH_2$), 4.17–4.30 (m, 3H, 4'-CH, 5'$CH_2$), 6.21 (t, 1H, 1'-CH), 8.04 (s, 1H, CH), 8.24 (s, 1H, CH).

Example 16

Prodrug of Timolol and 3,6-dioxaheptanoic Acid [(Scheme 5)]

The reaction scheme is illustrated in FIG. 5. 3,6-dioxaheptanoic acid (1.34 g), N-hydroxysuccinimide (1.15 g) and dicyclohexylcarbodiimide (2.063 g) were dissolved in 33 mL of anhydrous dichloromethane under argon. The resulting cloudy mixture was stirred at room temperature for 5 hours, filtered and evaporated to afford crude NHS ester of 3,6-dioxaheptanoic acid. Timolol (70 mg, free base) was dissolved in anhydrous dichloromethane (2 mL) and to this stirred solution at room temperature was added NHS ester of 3,6-dioxaheptanoic acid (51 mg). The homogenous reaction mixture was stirred at room temperature for 48 h, diluted with dichloromethane, washed 3 times with water, once with brine and dried over sodium sulfate. The crude product after solvent evaporation was purified by column chromatography on silica gel in chloroform-methanol, 30:1 to yield pure prodrug 25 (35 mg) as colorless oil. $^1H$ NMR ($CDCl_3$) δ 1.06 (s, 9H, t-Bu), 2.83 (d, 2H, $NCH_2$), 3.38 (s, 3H, $OCH_3$), 3.48 (m, 4H, 2×$NCH_2$), 3.57 (m, 2H, $OCH_2$), 3.72 (m, 2H, $OCH_2$) 3.79 (m, 4H, 2×$OCH_2$), 4.15 (d, 2H, $OCH_2$), 4.62 (m, 2H, $OCH_2$), 5.32 (m, 1H, OCH).

Example 17

Prodrug of Isoniazid and 3,6,9-trioxadecanoic Acid [(Scheme 13)]

The reaction scheme is illustrated in FIG. 13. To a stirred suspension of isoniazid (137 mg) in anhydrous acetonitrile (7 mL) was added pyridine (122 μL) followed by acid chloride prepared from 3,6,9-trioxadecanoic acid (295 mg). The reaction mixture was then stirred at room temperature overnight and evaporated to dryness to leave a yellow oily residue. This crude product was applied on a top of a silica gel column and a pure prodrug 48 was eluted using chloroform-methanol, 15:1. Yield of colorless oil was 185 mg. $^1H$ NMR ($CDCl_3$) δ 3.29 (s, 3H, $OCH_3$), 3.51 (m, 2H, $OCH_2$), 3.67 (m, 4H, 2×$OCH_2$), 3.78 (m, 2H, $OCH_2$), 4.18 (s, 2H, $OCH_2$), 7.61 (d, 2H, pyridine), 8.61 (d, 2H, pyridine), 9.60 (s, 1H, NH), 10.54 (s, 1H, NH).

Example 18

Prodrug of Zidovudine and 3,6-dioxaheptanoic Acid [(Scheme 9)]

Figure 9:
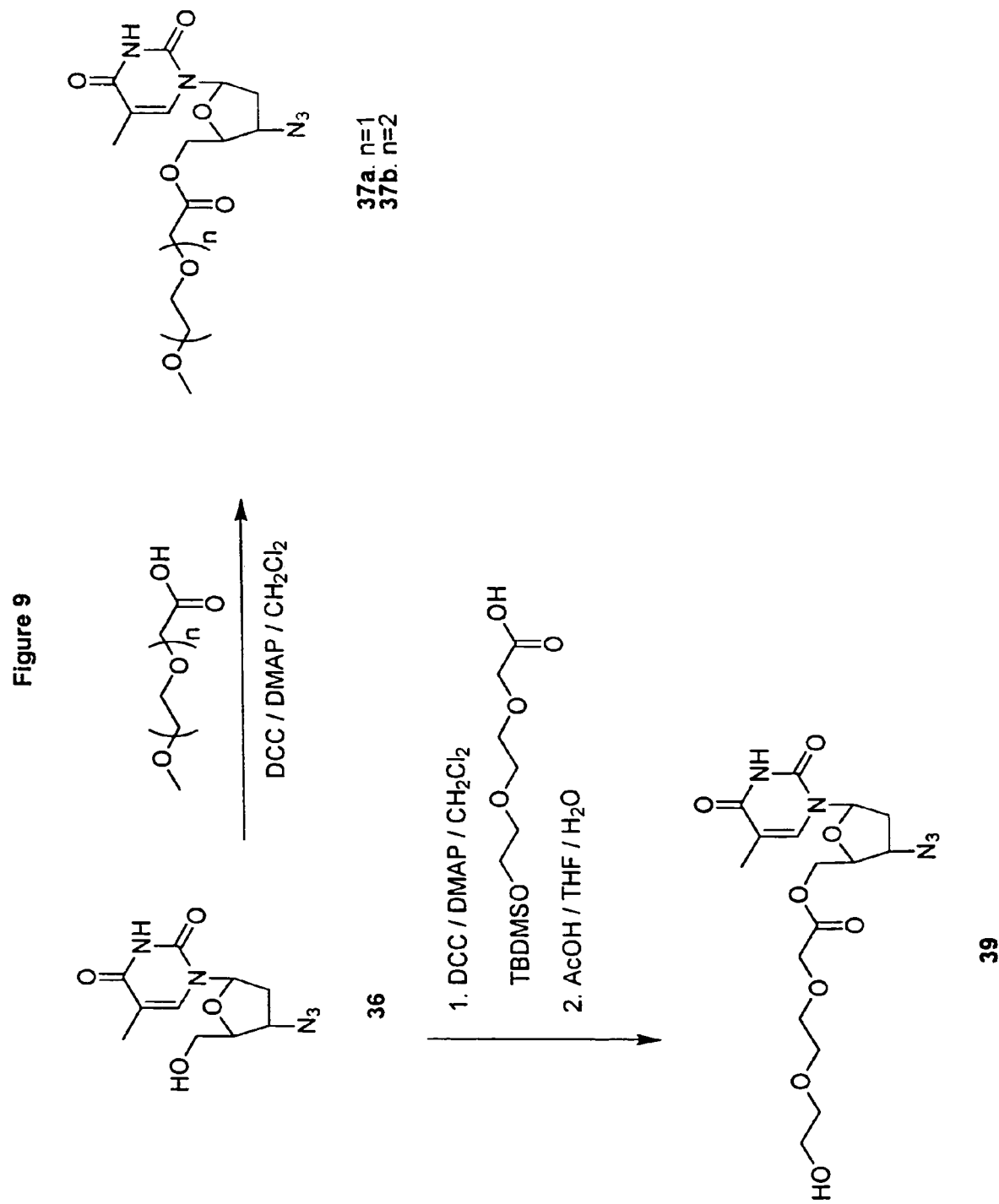

The reaction scheme is illustrated in FIG. 9. Zidovudine (80 mg) and 3,6-dioxaheptanoic acid were dissolved in a mixture of dichloromethane (1.5 mL) and acetonitrile (0.5 mL) at room temperature. To the resulting solution was added dicyclohexylcarbodiimide (80 mg) followed by catalytical amount of DMAP. The resulting cloudy mixture was stirred at room temperature overnight and then was evaporated to dryness under vacuum. The oily residue was absorbed on silica gel and chromatographed in chloroform-methanol, 45:1 to afford 112 mg of pure prodrug 37a as colorless oil. $^1H$ NMR ($CDCl_3$) δ 1.93 (s, 3H, $CCH_3$), 2.45 (t, 2H, 2'-$CH_2$), 3.36 (s, 3H, $OCH_3$), 3.58 (m, 2H, $OCH_2$), 3.73 (m, 2H, $OCH_2$), 4.08 (m, 1H, 3'-CH), 4.24 (d, 2H, $OCH_2$), 4.28 (m, 1H, 4'-CH), 4.42 (d, 2H, 5'-$CH_2$), 6.15 (t, 1H, 1'-CH), 7.26 (d, 1H, 6-CH), 9.65 (s, 1H, NH).

Example 19

Prodrug of Zidovudine and 3,6,9-trioxadecanoic Acid [(Scheme 9)]

The reaction scheme is illustrated in FIG. 9. The reaction was performed as described in example 18 using 80 mg of zidovudine, 69 mg of 3,6,9-trioxadecanoic acid and 80 mg of dicyclohexylcarbodiimide. The product 37b was obtained as colorless oil (137 mg). $^1H$ NMR ($CDCl_3$) δ 1.93 (s, 3H, $CCH_3$), 2.46 (t, 2H, 2'-$CH_2$), 3.37 (s, 3H, $OCH_3$), 3.51–3.80 (4m, 8H, 4×$OCH_2$), 4.08 (q, 1H, 3'-CH), 4.24 (d, 2H, $OCH_2$), 4.28 (m, 1H, 4'-CH), 4.41 (d, 2H, 5'-$CH_2$), 6.14 (t, 1H, 1'-CH), 7.25 (d, 1H, 6-CH), 9.62 (s, 1H, NH).

Example 20

Prodrug of DDC and (2-aminoethoxy)acetic Acid [(Scheme 8)]

Figure 8:
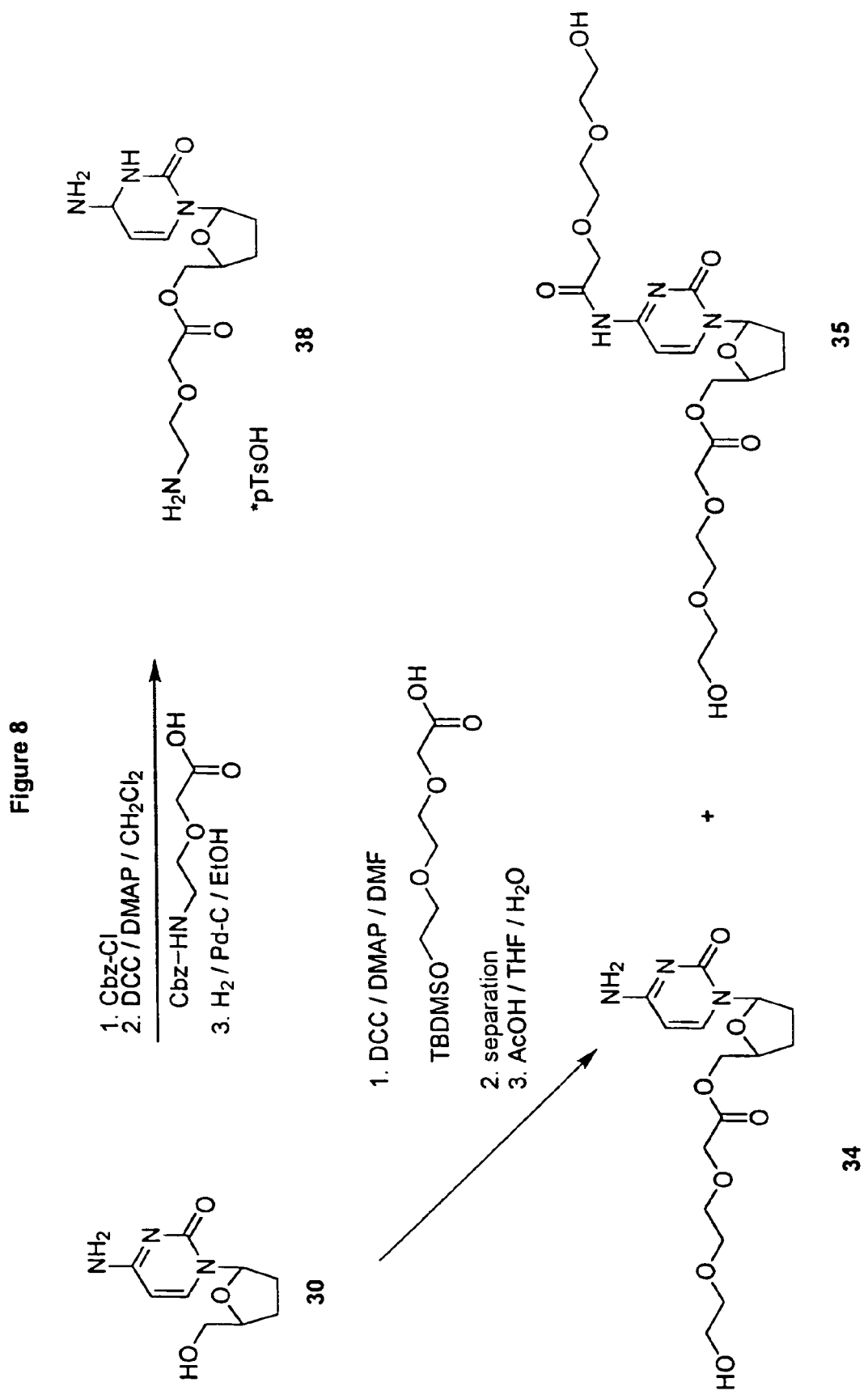

The reaction scheme is illustrated in FIG. 8. N-benzyloxycarbonyl-DDC (109 mg) and (N-benzyloxycarbonyl-2-aminoethoxy)acetic acid (120 mg) were dissolved in 2 ml of anhydrous dichloromethane at room temperature. To the resulting solution was added dicyclohexylcarbodiimide (98 mg) followed by catalytical amount of DMAP. The resulting cloudy mixture was stirred at room temperature overnight, filtered, diluted with 10 mL of dichloromethane and washed subsequently with 1M hydrochloric acid, aqueous sodium bicarbonate and brine. An organic extract was dried over sodium sulfate and evaporated to leave a yellow oily residue. The product was purified by column chromatography on silica gel using chloroform-methanol, 45:1 as a solvent system. 119 mg of pure bis-protected ester was isolated. This product was dissolved in absolute ethanol (8 mL) and hydrogenated over 10% Pd—C (15 mg) in Paar apparatus for 5 hr. Filtration and solvent evaporation left 74 mg of colorless oil which was dissolved in small amount of methanol and an equivalent of p-toluenesulfonic acid in methanol was added. The solution was evaporated to dryness and the residue was precipitated with cold ethyl ether to afford a colorless solid of prodrug 38 (65 mg). $^1$H NMR of free base (CDCl$_3$) δ 1.65, 1.98, 2.14, 2.50 (4m, 4H, 2'-CH$_2$, 3'-CH$_2$), 3.12 (m, 2H, NCH$_2$), 3.64 (t, 2H, OCH$_2$), 4.16 (s, 2H, OCH$_2$), 4.34 (m, 1H, 4'-CH), 4.42 (m, 2H, 5'CH$_2$), 5.10, (s, 1H, CH), 5.18, (s, 1H, CH), 6.01 (m, 1H, 1'-CH).

Example 21

Prodrug of Saquinavir with Diglycolic Acid [(Scheme 11)]

Figure 11:
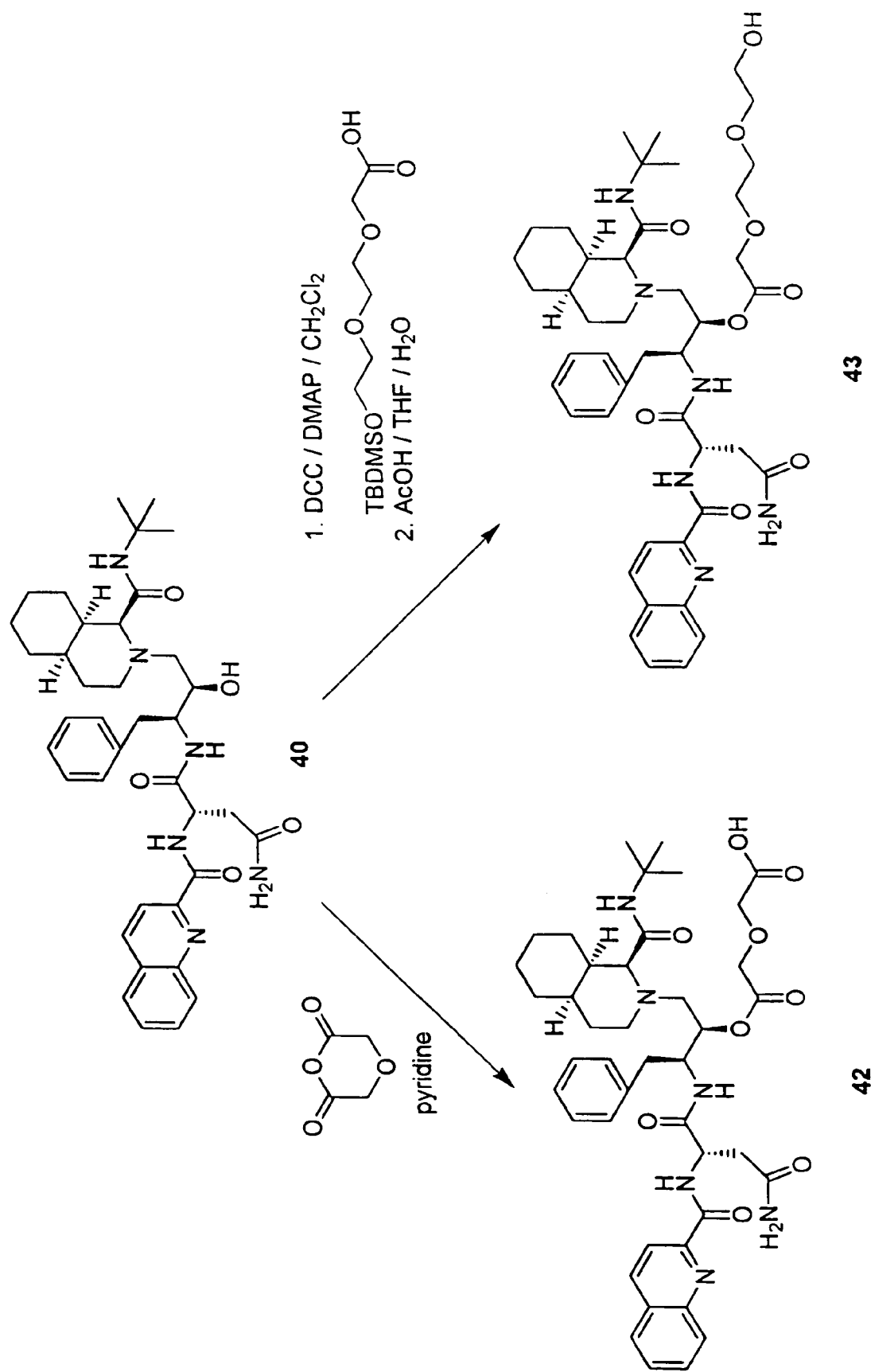

The reaction scheme is illustrated in FIG. 11. To a stirred solution of saquinavir (55 mg) in anhydrous pyridine (1 mL) was added 19 mg of diglycolic anhydride and the mixture was stirred under argon at 50° C. overnight. The cooled reaction mixture was slowly added to a mixture of hexane-ethyl ether, 1:1 (50 mL) at 0° C. The precipitated product was filtered off and washed with hexane-ether mixture. The colorless solid prodrug 42 was dried under high vacuum. Yield 53 mg. $^1$H NMR (CDCl$_3$) δ 1.34 (s, 9H, t-BU), 4.18–4.50 (m, 5H, OCH$_2$, OCH$_2$, NHCH), 5.54 (m, 1H, CH—OOC), 7.15 (m, 5H, Ph), 7.60–8.30 (m, 6H, quinoline).

Example 22

Prodrug of Saquinavir and 8-hydroxy-3,6-dioxaoctanoic Acid [(Scheme 11)]

The reaction scheme is illustrated in FIG. 11. To a stirred solution of saquinavir (56 mg) and O-silylated 8-hydroxy-3,6-dioxaoctanoic acid (31 mg) in 2 mL of anhydrous acetonitrile under argon was added dicyclohexylcarbodiimide (22 mg) followed by DMAP (catalytical amount). After a few minutes the reaction mixture turned cloudy and was stirred at room temperature overnight. The mixture was then filtered and evaporated to dryness. The residue was dissolved in dichloromethane (20 mL), washed once with water, once with sodium bicarbonate solution and once with brine. Drying over sodium sulfate followed by solvent evaporation left crude product, which was purified by preparative TLC in chloroform-methanol, 30:1. The above protected product (47 mg) was dissolved in 2 mL of a mixture of acetic acid-THF-water (3:1:1). The resulting homogeneous solution was left at room temperature overnight and the solvents were evaporated to dryness. The residue was dissolved in dichloromethane (20 mL), washed with water (2×5 mL), brine (5 mL) and dried over sodium sulfate. Solvent evaporation afforded 37 mg of crude product with was purified by preparative TLC in chloroform-methanol, 12:1. The pure codrug 43 was obtained as colorless foam (30 mg). $^1$H NMR (CDCl$_3$) δ 1.36 (s, 9H, t-Bu), 3.60–3.84. (m, 8H, 4×OCH$_2$), 4.24 (dd, 2H, OCH$_2$CO), 4.46 (m, 1H, CH), 4.83 (m, 1H, CH), 5.54 (m, 1H, CH—OOC), 7.15 (m, 5H, Ph), 7.57–8.52 (m, 6H, quinoline).

Example 23

Prodrug of Saquinavir and 3,6-dioxaheptanoic Acid [(Scheme 10)]

Figure 10:
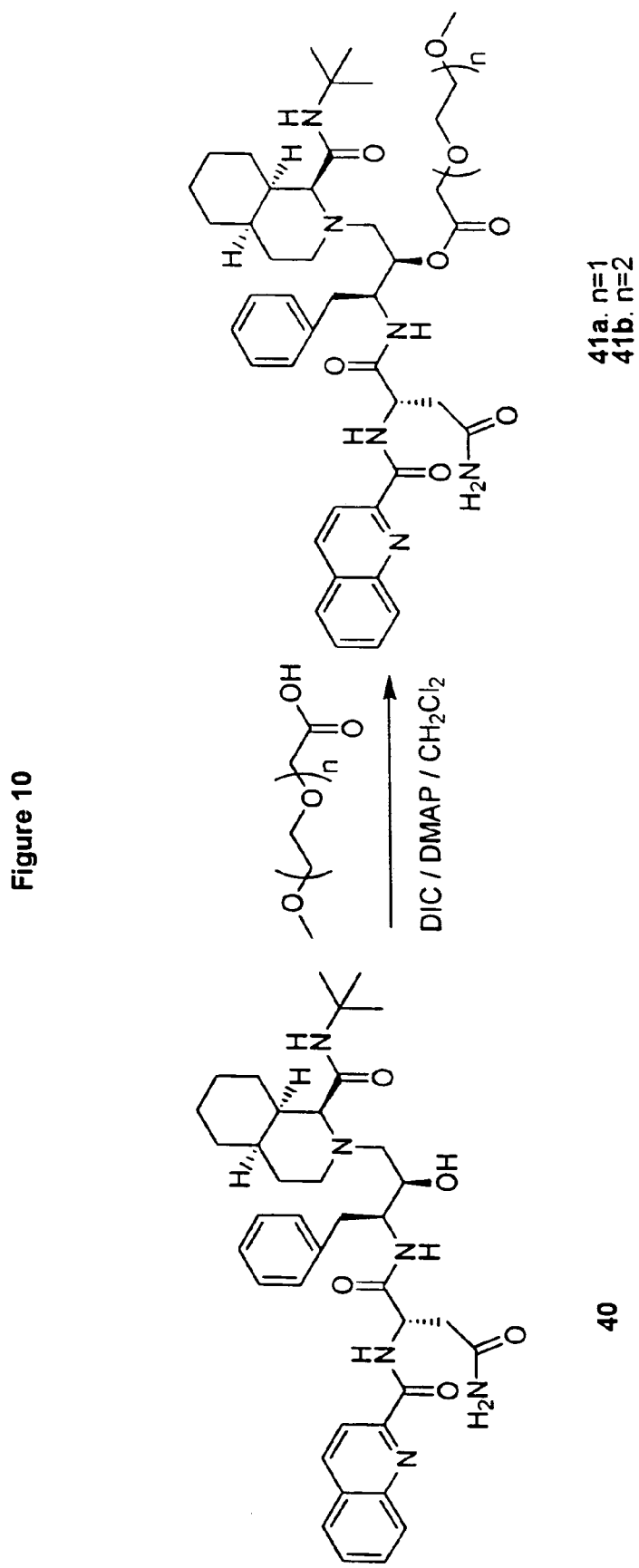

The reaction scheme is illustrated in FIG. 10. To a stirred solution of 3,6-dioxaheptanoic acid (12 mg) in dichloromethane (2 mL) was added saquinavir (40 mg) followed by diisopropylcarbodiimide (14 μL) and catalytical amount of DMAP. The resulting solution was stirred at room temperature overnight, 15 mL of dichloromethane was added and the organic solution was washed twice with water (2×4 mL), brine (5 mL) and dried over sodium sulfate. Evaporation of the solvent yielded 65 mg of crude material, which was purified by column chromatography on silica gel using chloroform-methanol, 38:1, to afford 42 mg of pure prodrug 41a as colorless powder. $^1$H NMR (CDCl$_3$) δ 1.36 (s, 9H, t-Bu), 3.37 (s, 3H, OCH$_3$), 5.50 (m, 1H, CH—OOC), 7.16 (m, 5H, Ph), 7.60–8.30 (m, 6H, quinoline).

Example 24

Prodrug of Saquinavir and 3,6,9-trioxadecanoic Acid [(Scheme 10)]

The reaction scheme is illustrated in FIG. 10. The synthesis of the prodrug was performed as described above in example 23. From 40 mg of saquinavir, 18 mg of 3,6,9-trioxadecanoic acid, 14 μL of diisopropylcarbodiimide in 2 mL of anhydrous dichloromethane was obtained 42 mg of the prodrug 41b after chromatographic purification. $^1$H NMR (CDCl$_3$) δ 1.37 (s, 9H, t-Bu), 3.35 (s, 3H, OCH$_3$), 5.50 (m, 1H, CH—OOC), 7.16 (m, 5H, Ph), 7.58–8.30 (m, 6H, quinoline).

Example 25

Prodrug of Ritonavir and Diglycolic Acid [(Scheme 12)]

Figure 12:
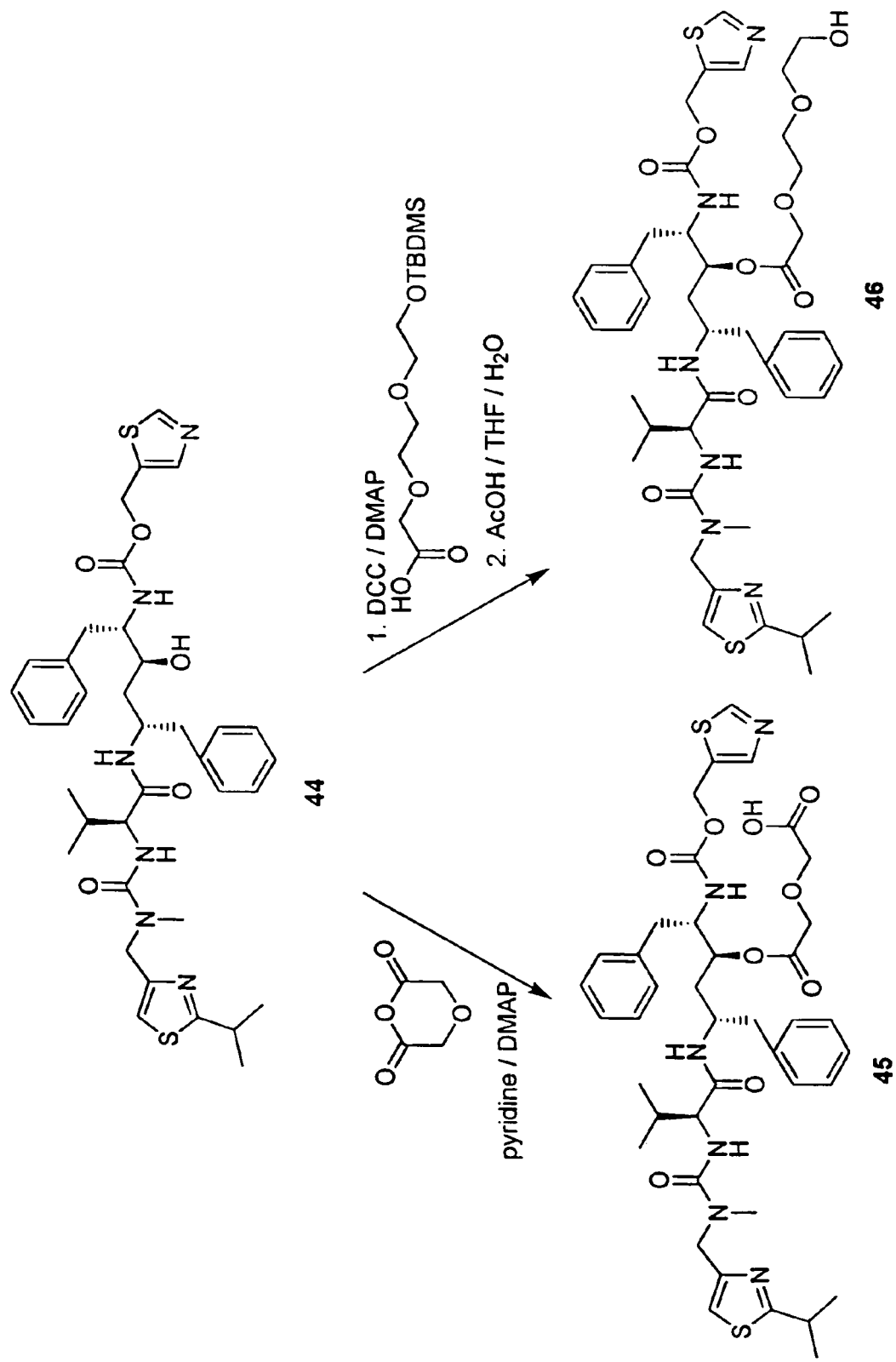
Figure 14:
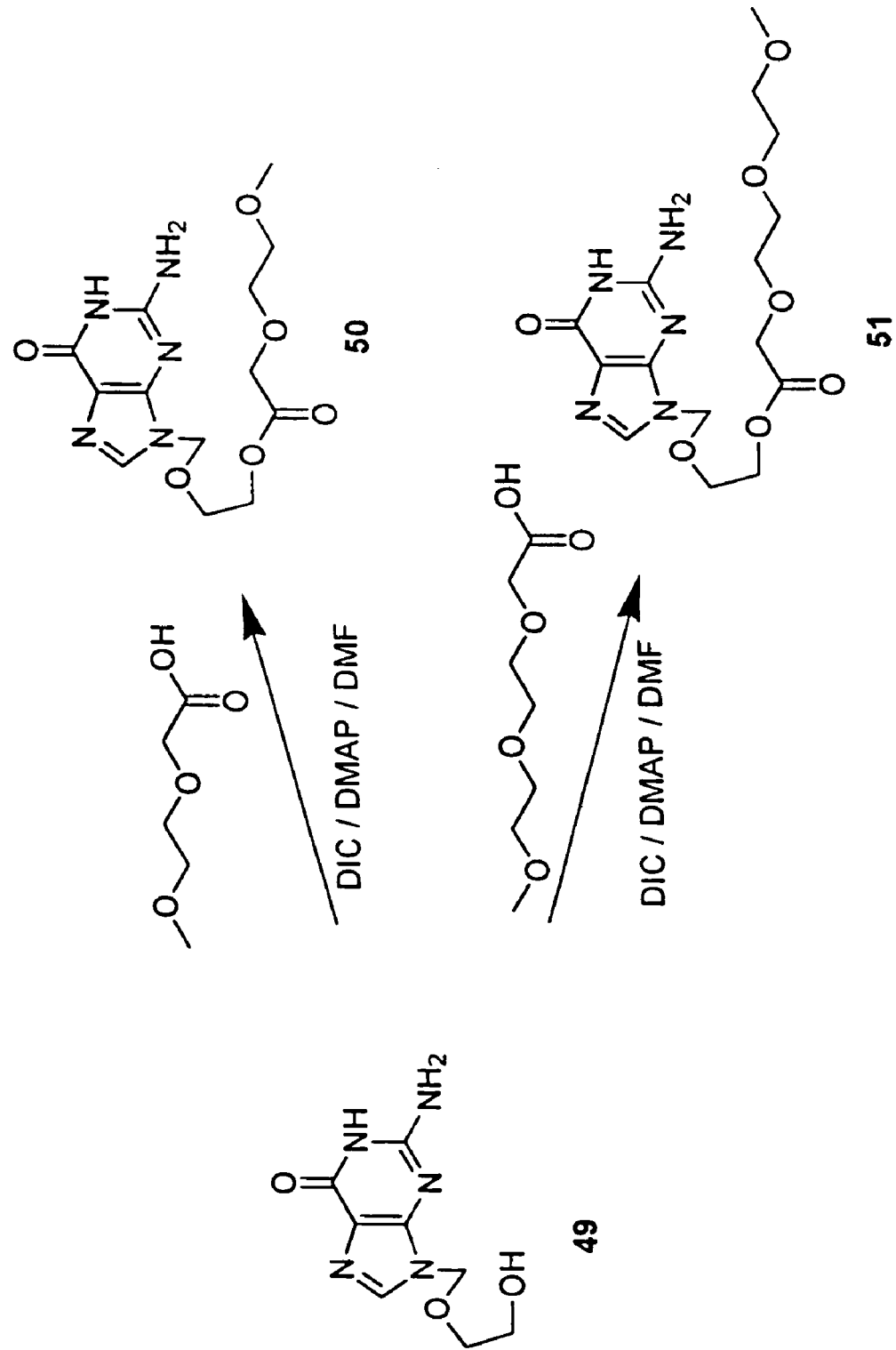
Figure 15:
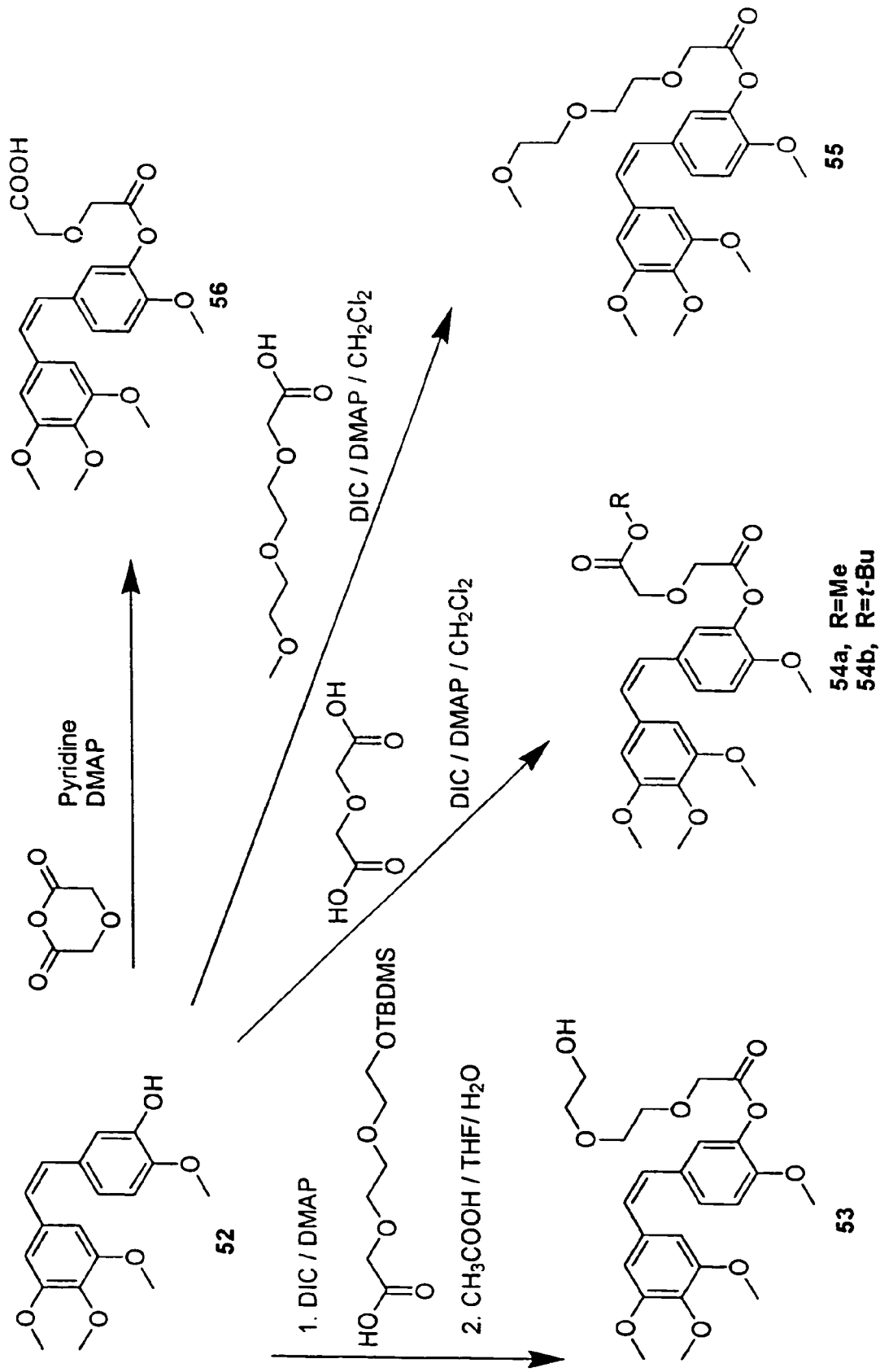
Figure 16:
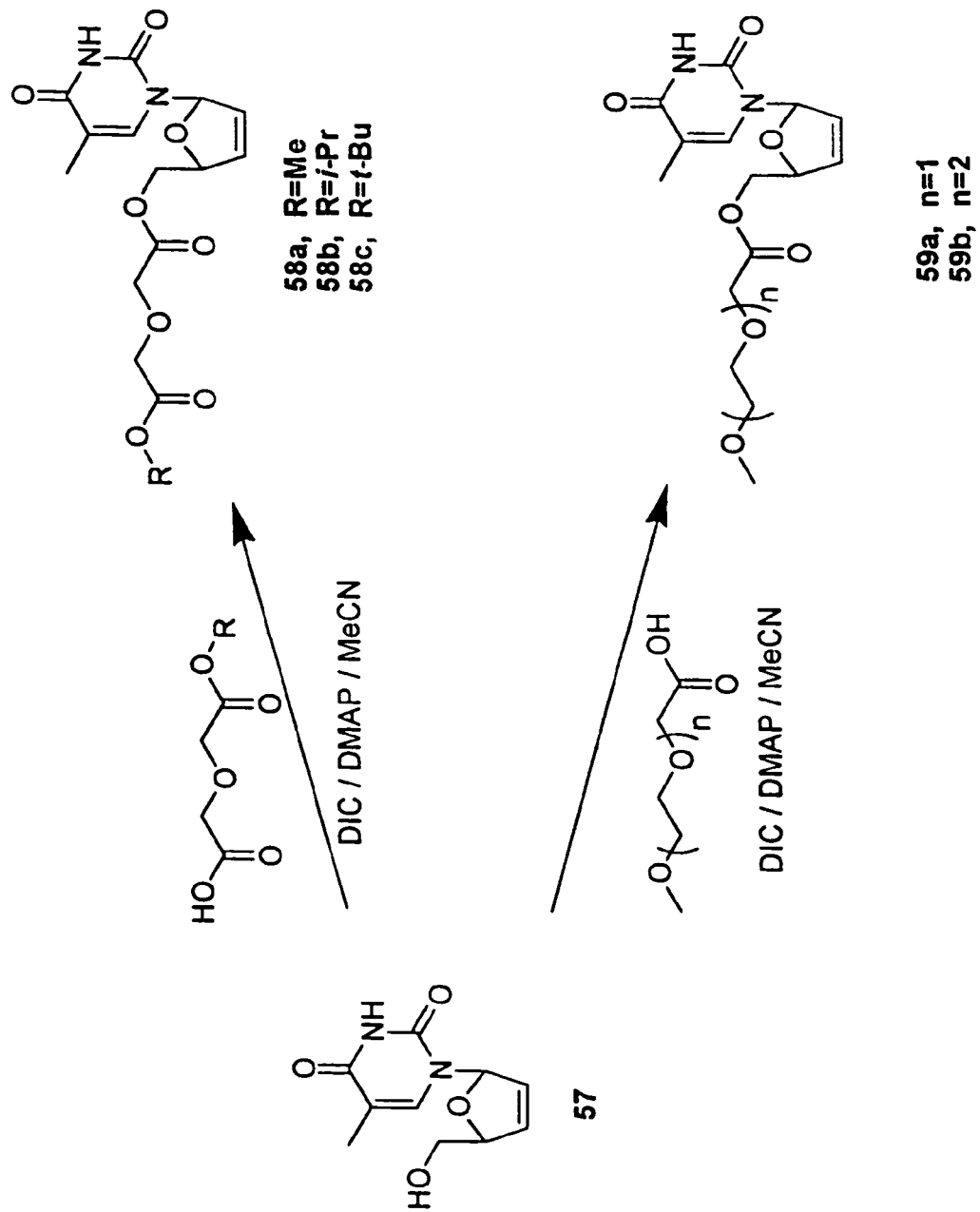
Figure 17:
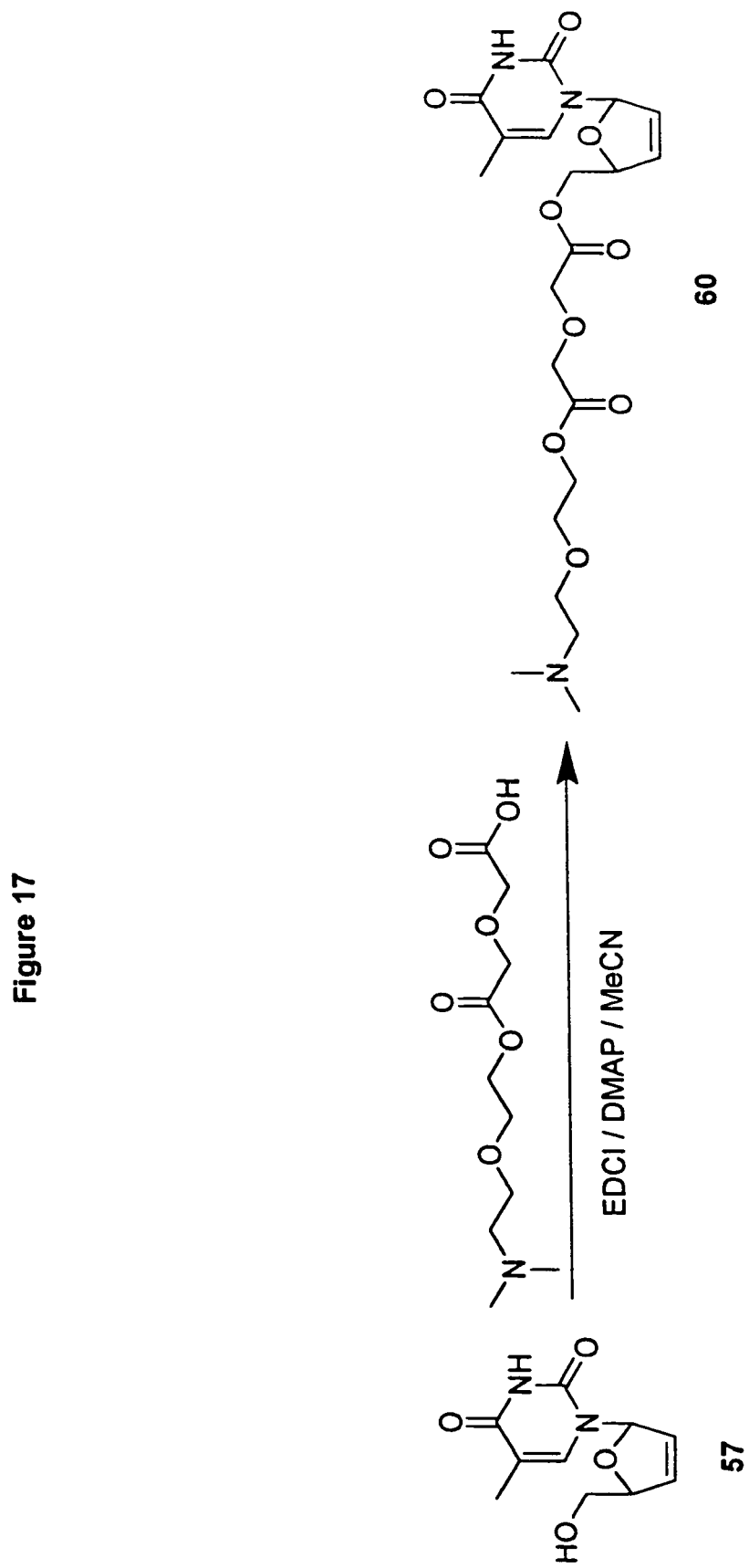
Figure 18:
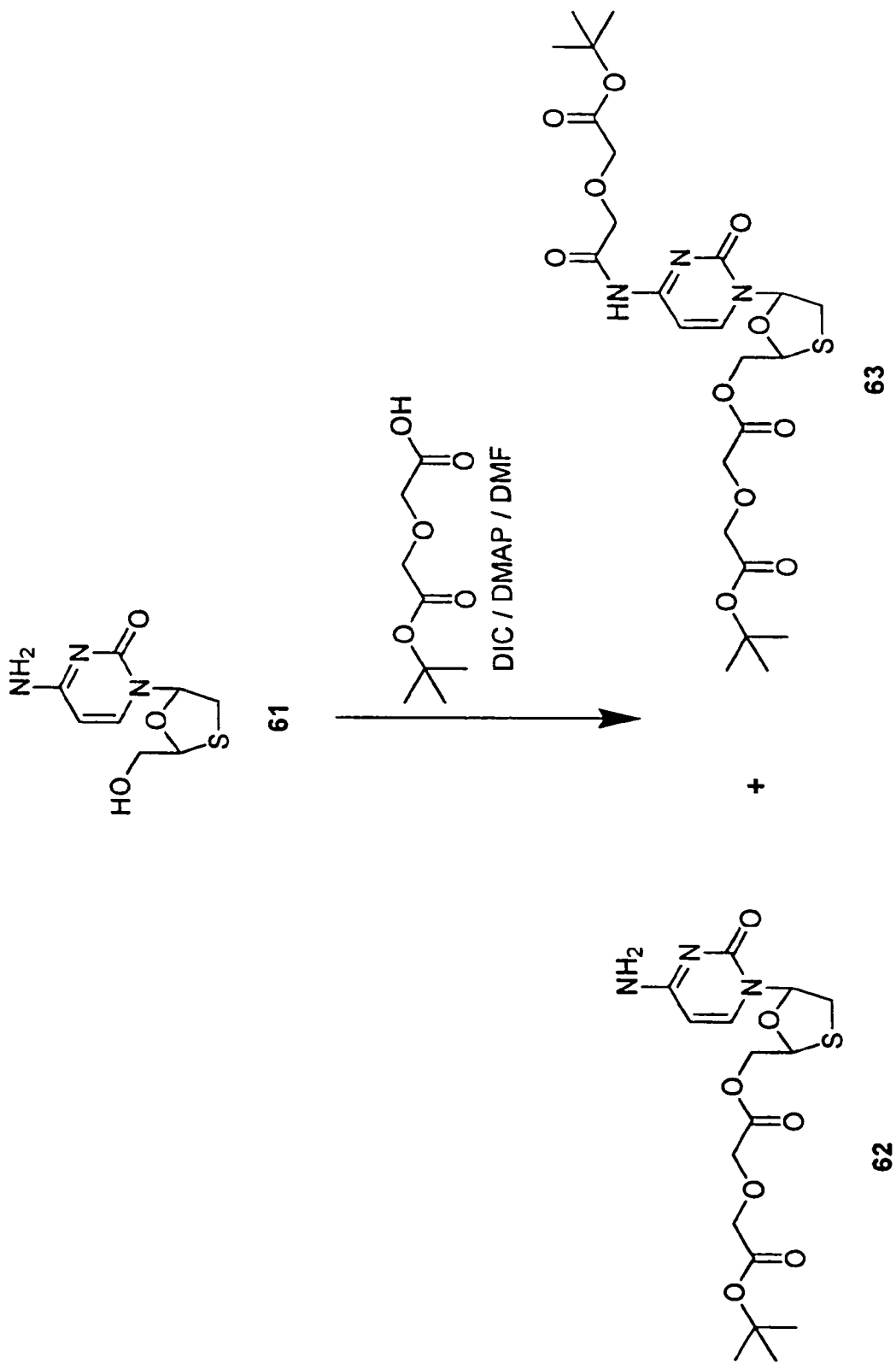
Figure 19:
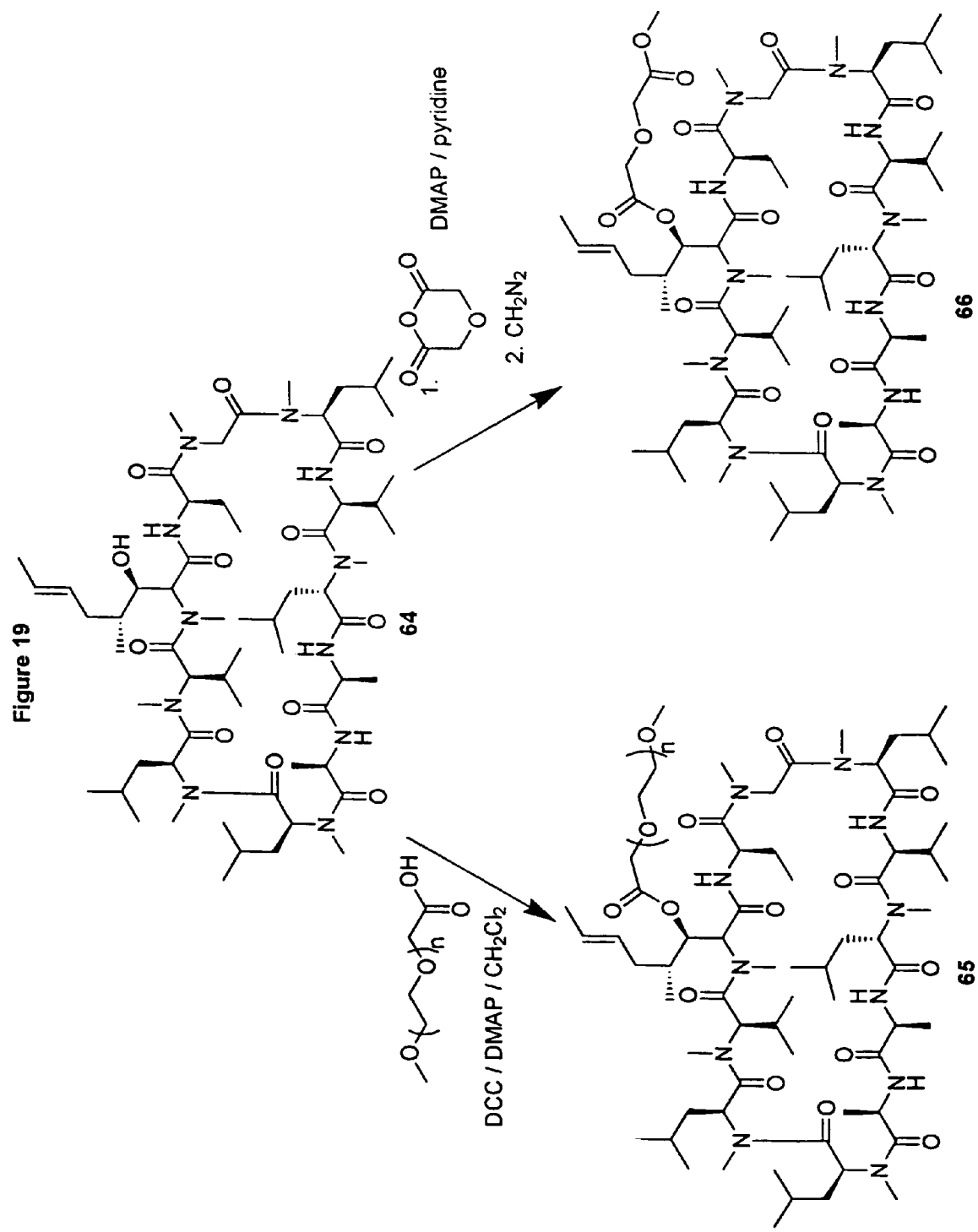
Figure 20:
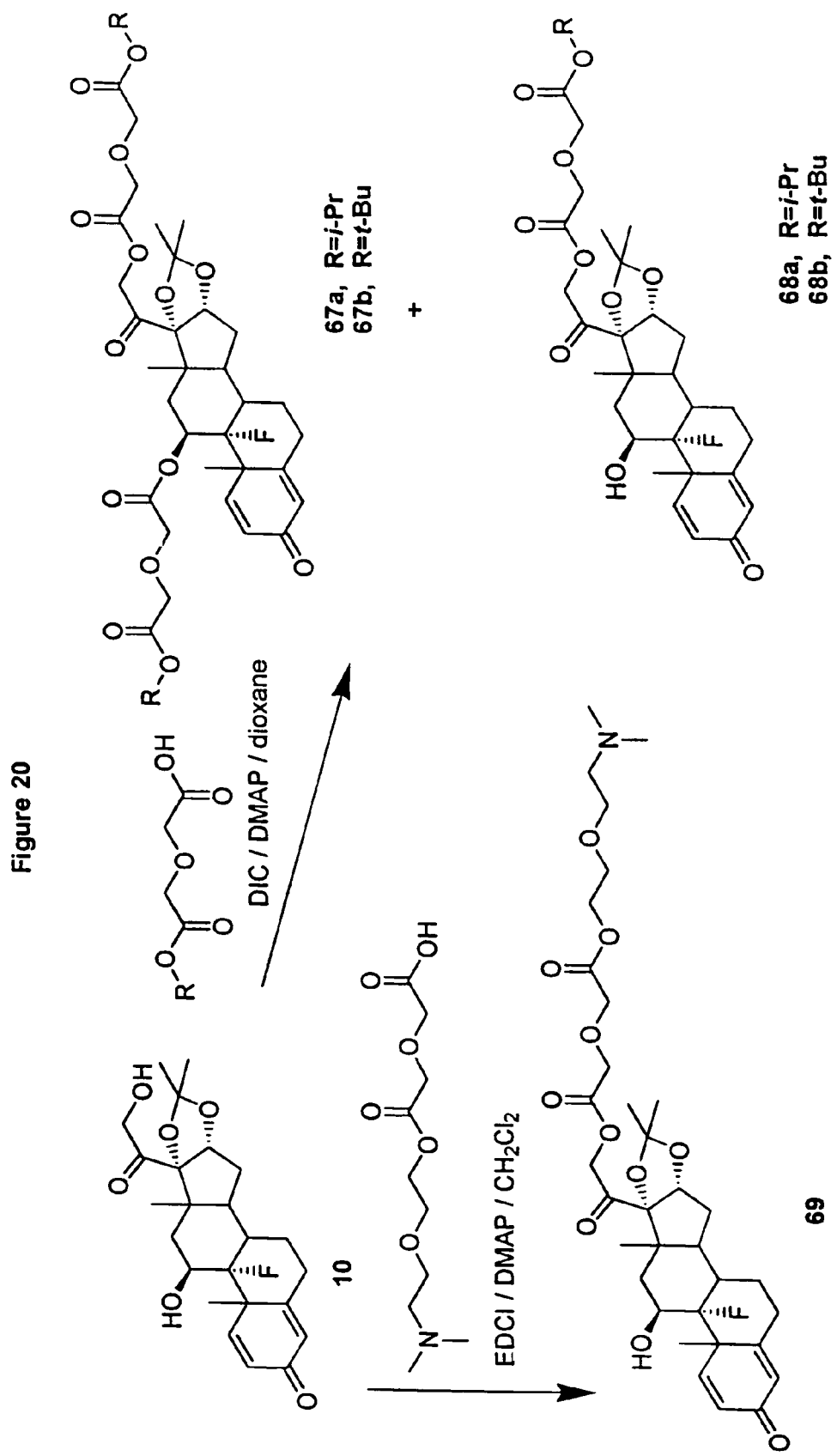
Figure 21:
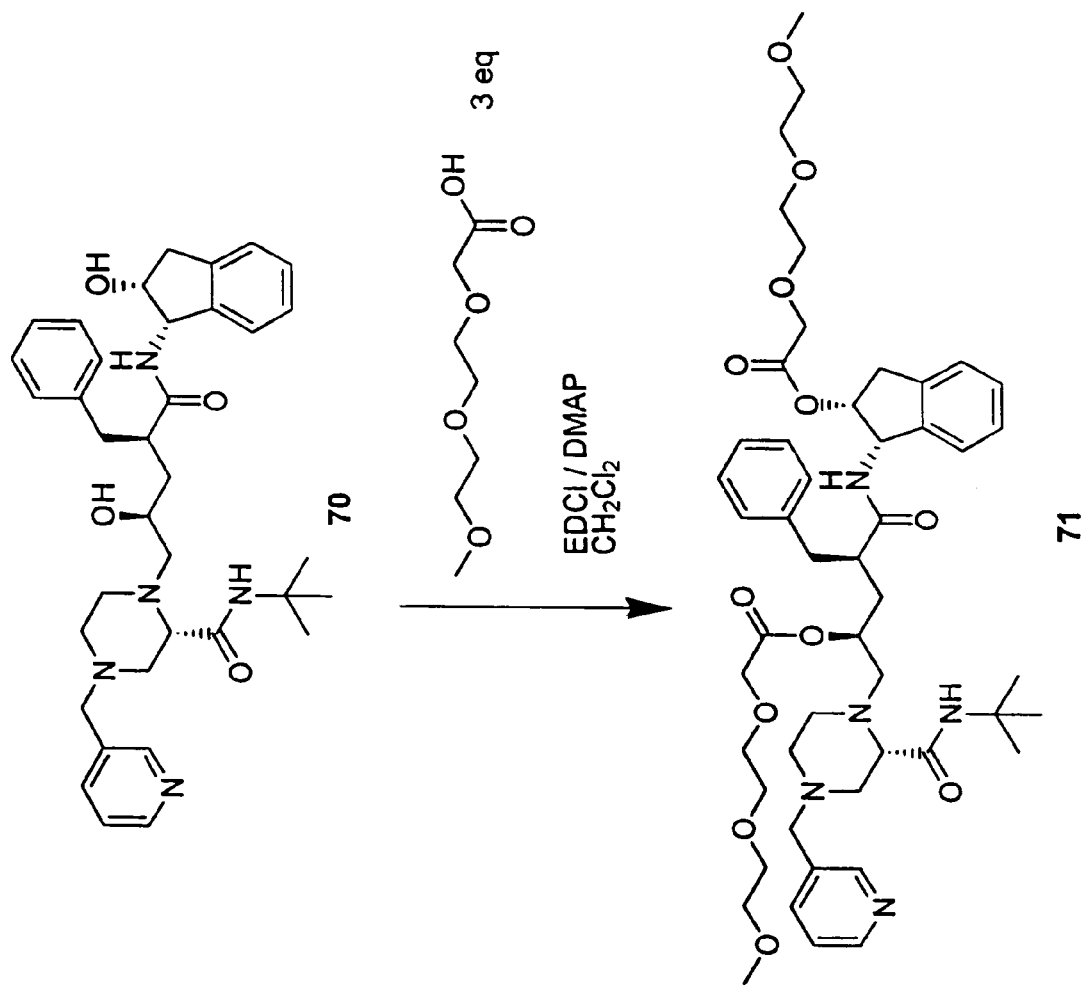
Figure 22:
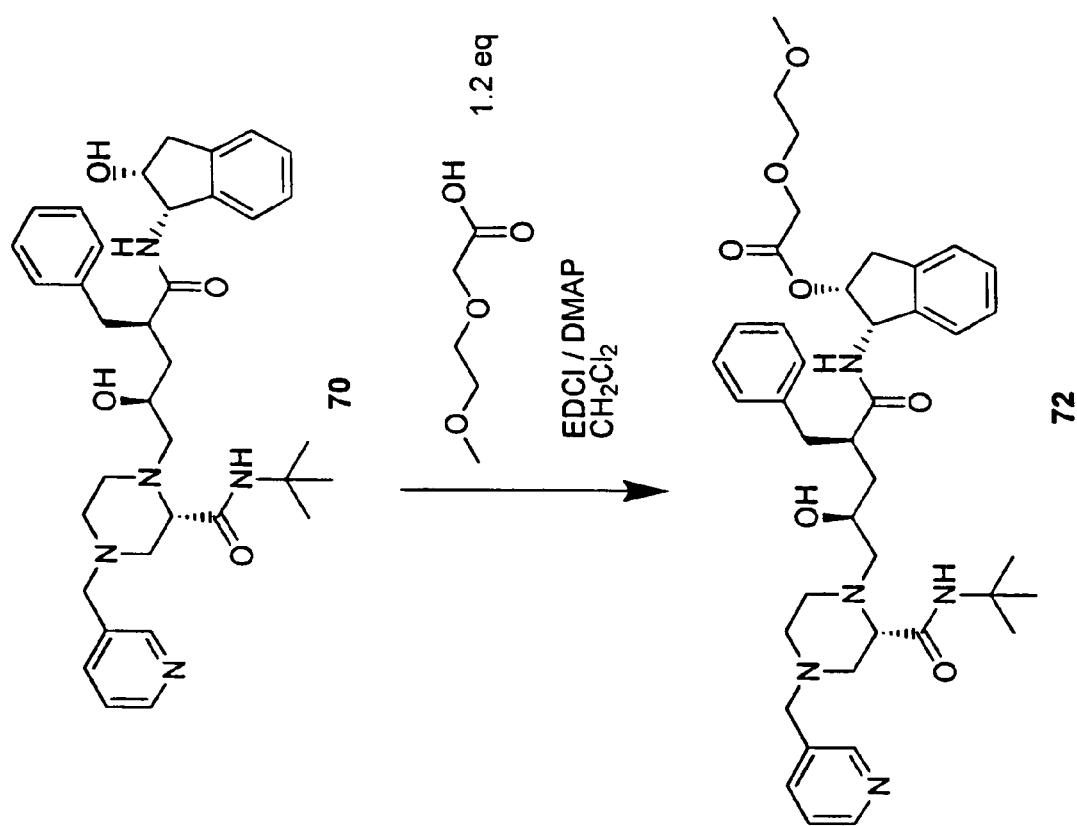
Figure 23:
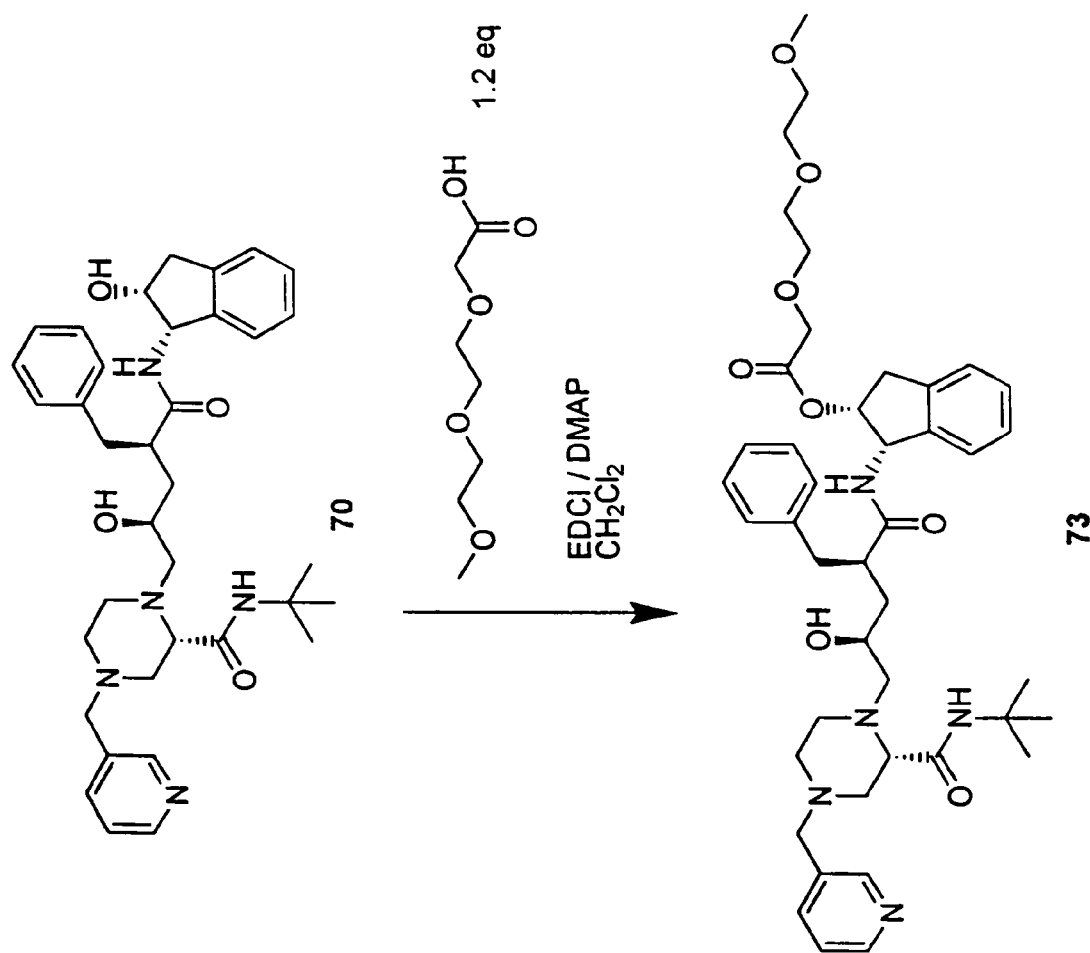

The reaction scheme is illustrated in FIG. 12. To a solution of ritonavir (50 mg) in anhydrous pyridine (1 mL) under argon was added diglycolic anhydride followed by DMAP (5 mg). The resulting homogenous solution was stirred at room temperature overnight. Pyridine was evaporated under vacuum and the residue was dissolved in chloroform (10 mL). The solution was washed with 0.5M HCl, water, brine and dried Na$_2$SO$_4$. The extract was concentrated to a small volume and the solution was poured into excess of cold ethyl ether. The resulting precipitated prodrug 45 was filtered off and dried under high vacuum. Yield 39 mg. $^1$H NMR (CDCl$_3$) δ 0.86 (m, 6H, isopropyl), 1.36 (d, 6H, isopropyl), 2.96 (s, 3H, NCH$_3$), 4.22, 4.41 (2s, 4H, 2×OCH$_2$), 5.15 (d, 2H, CH$_2$), 6.96–7.26 (m, 11H, 2×Ph, CH), 7.78 (s, 1H, CH), 8.77 (s, 1H, CH).

Example 26

Prodrug of Ritonavir and 8-hydroxy-3,6-dioxaoctanoic Acid [(Scheme 12)]

The reaction scheme is illustrated in FIG. 12. To a stirred solution of ritonavir (165 mg) in anhydrous acetonitrile (4 mL) was added O-silylated 8-hydroxy-3,6-dioxaoctanoic acid (86 mg) followed by dicyclohexylcarbodiimide (61 mg) and DMAP (3 mg). The resulting cloudy mixture was stirred at room temperature under argon overnight. The mixture was filtered and evaporated to dryness. The resulting foam was dissolved in dichloromethane (20 mL) and the solution was washed with water, aqueous sodium bicarbonate, water and brine. Drying over sodium sulfate followed by solvent evaporation afforded 230 mg of colorless oil, which was purified by column chromatography on silica gel using chloroform-methanol, 35:1 as a solvent system. The pure ester thus obtained was dissolved in a mixture of acetic acid, THF and water (3:1:1, 2 mL. The resulting solution was stirred at room temperature for 70 min and the solvents were removed under vacuum. The crude product was separated by column chromatography on silica gel affording 82 mg of pure prodrug 46. $^1$H NMR (CDCl$_3$) δ 0.84 (2d, 6H, isopropyl), 1.39 (d, 6H, isopropyl), 2.73 (m, 4H, 2×CH$_2$), 2.99 (s, 3H, NCH$_3$), 5.17 (d, 2H, CH$_2$), 7.03–7.27 (m, 11H, 2×Ph, CH), 7.80 (s, 1H, CH), 8.79 (s, 1H, CH).

Specific compounds according to the present invention, together with some half-life data of hydrolysis of the prodrugs in human serum and phosphate buffer at pJ 7.4 is shown in Table 1.

TABLE 1

Half-lives of hydrolysis of the prodrugs in human serum and phosphate buffer at ph 7.4

| Structure | Serum | Buffer |
|---|---|---|
| 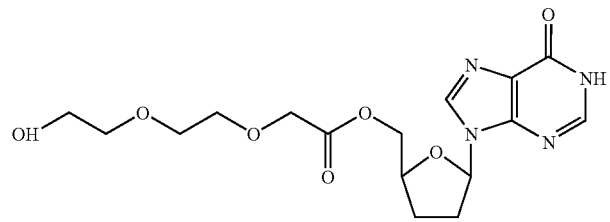 | 5.5 ± 0.5 min | 46 hr |
| 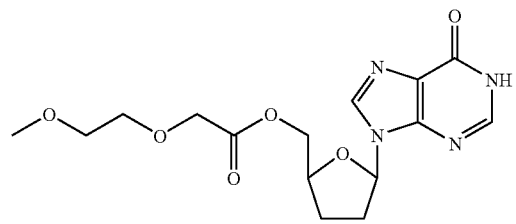 | 2.2 min | 40 hr |
| 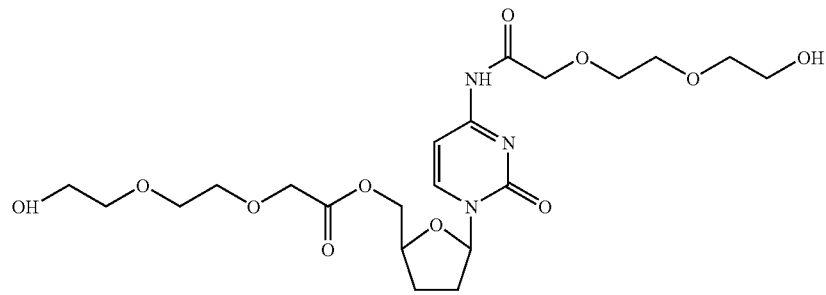 | 5.0 ± 1.0 min (to mono) | 20 hr (to mono) |
| 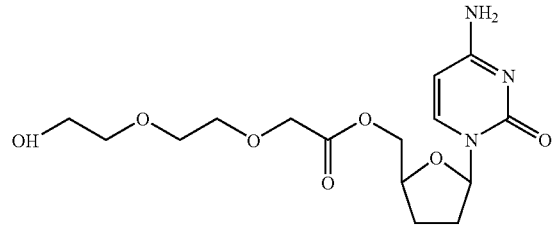 | 10.0 ± 1.0 min | 30 hr |
| 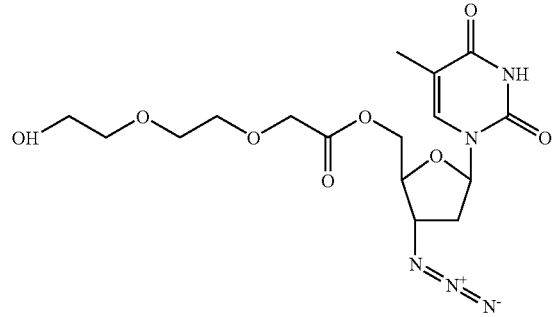 | 20.0 ± 1.0 min | 21 hr |

TABLE 1-continued
Half-lives of hydrolysis of the prodrugs in human serum and phosphate buffer at ph 7.4
| Structure | Serum | Buffer |
|---|---|---|
| 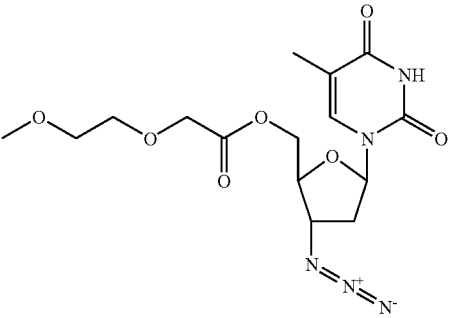 | 3.6 ± 0.1 min | 13.3 ± 0.2 hr |
| 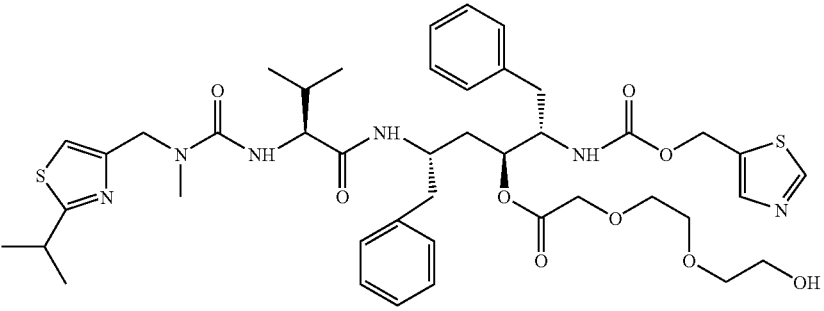 | 24 hr | 96 hr |
| 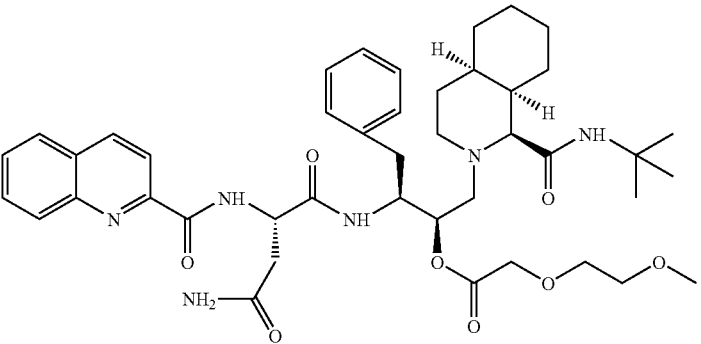 | 16.0 ± 1.0 hr | 3.2 ± 0.5 hr |
| 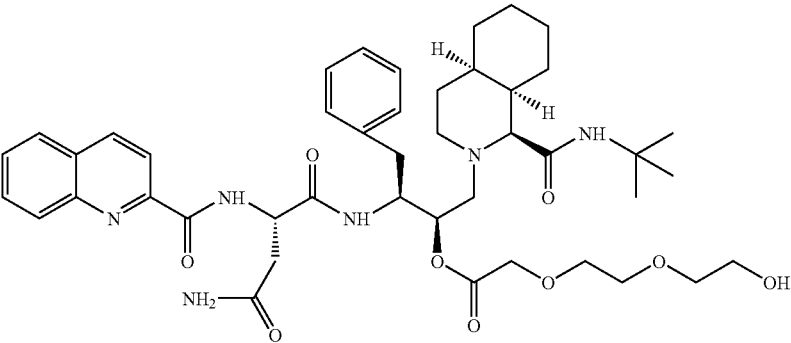 | 6.0 ± 0.5 hr | 3.1 ± 0.1 hr |

TABLE 1-continued
Half-lives of hydrolysis of the prodrugs in human serum and phosphate buffer at ph 7.4
| Structure | Serum | Buffer |
|---|---|---|
| 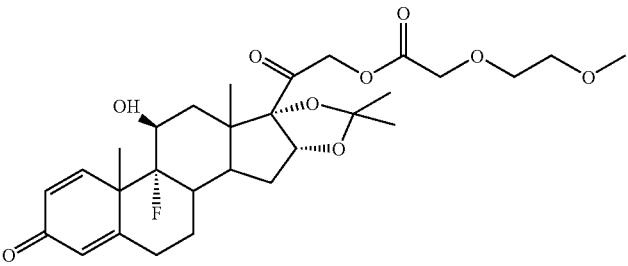 | 6 min | 15 hr |
| 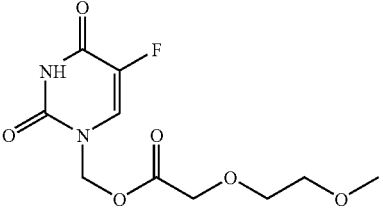 | 6.0 min | 88 min |
| 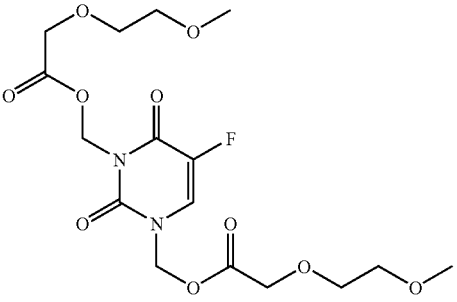 | 0.2 min (to mono) | 88 min (to mono) |
| 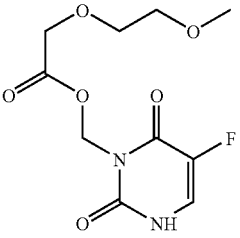 | 0.5 min | 546 min |
| 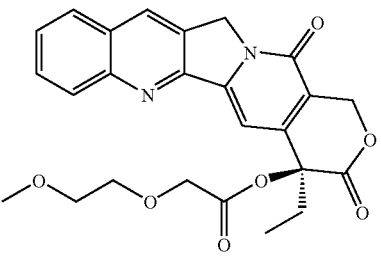 | 2 hr | 26 hr |

TABLE 1-continued
Half-lives of hydrolysis of the prodrugs in human serum and phosphate buffer at ph 7.4
| Structure | Serum | Buffer |
|---|---|---|
| 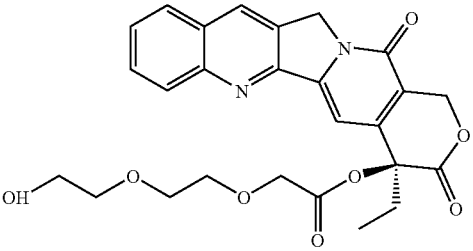 | 1.9 hr | 30 hr |
| 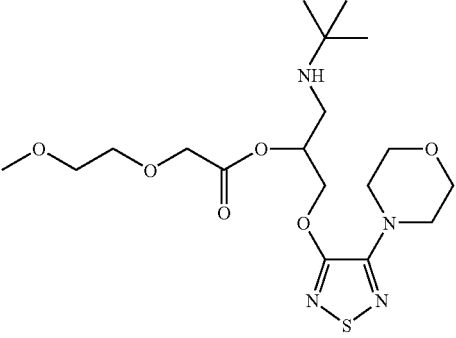 | | |
| 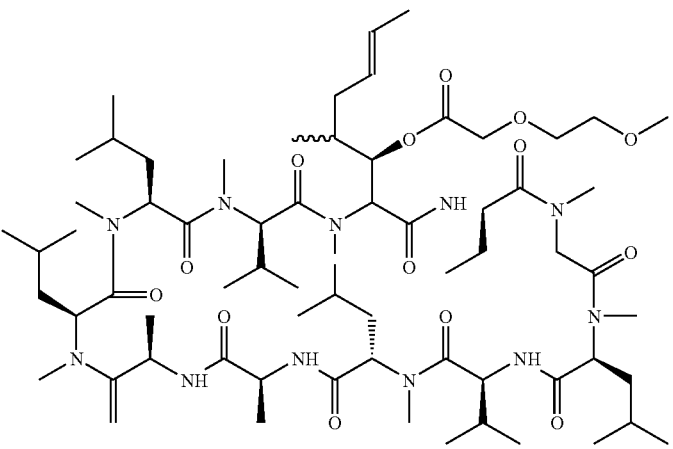 | stable | stable |
| 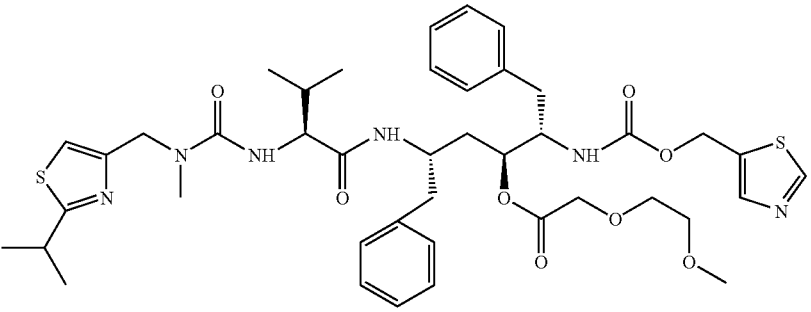 | 24 hr | >2 days |

TABLE 1-continued

Half-lives of hydrolysis of the prodrugs in human serum and phosphate buffer at ph 7.4

| Structure | Serum | Buffer |
|---|---|---|
| 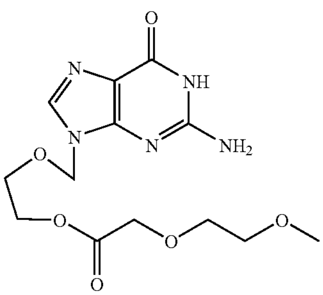 | 5.5 min | 30 hr |

TABLE 1-continued
Half-lives of hydrolysis of the prodrugs in human serum and phosphate buffer at ph 7.4
| Structure | Serum | Buffer |
|---|---|---|
| 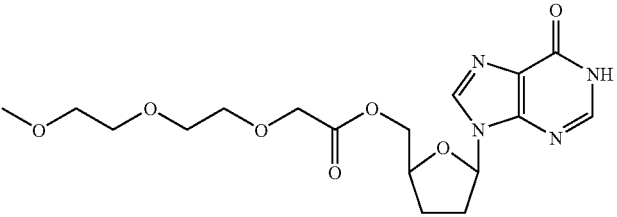 | 1.2 min | 30 hr |
| 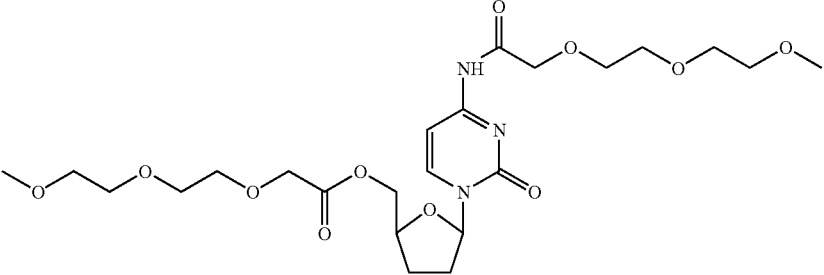 | 35.0 ± 5.0 min | 14.0 ± 1.0 hr |
| 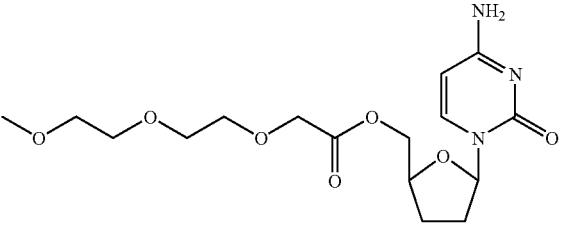 | 4.5 min | 24 hr |
| 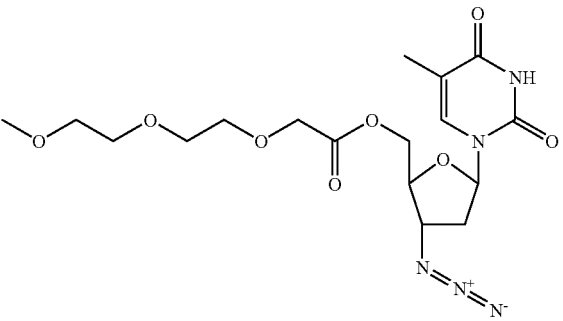 | 24.2 ± 0.2 min | 12.3 ± 0.1 hr |
| 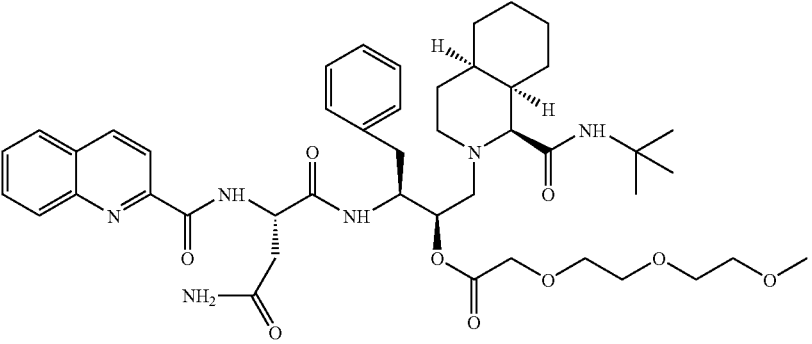 | 10.0 ± 1.0 hr | 3.5 ± 0.2 hr |

TABLE 1-continued
Half-lives of hydrolysis of the prodrugs in human serum and phosphate buffer at ph 7.4
| Structure | Serum | Buffer |
|---|---|---|
| 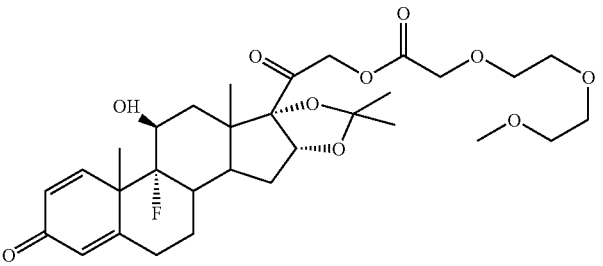 | 62 min | 12 hr |
| 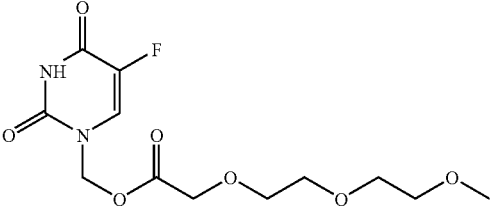 | 9.0 min | 224 min |
| 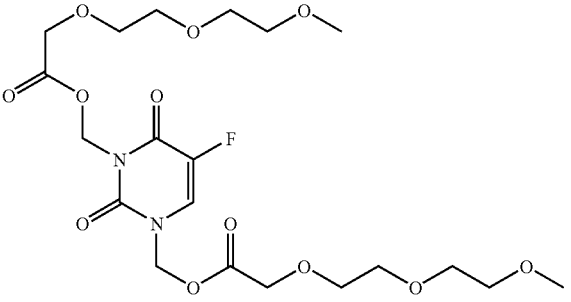 | 0.5 min (to mono) | 88 min (to mono) |
| 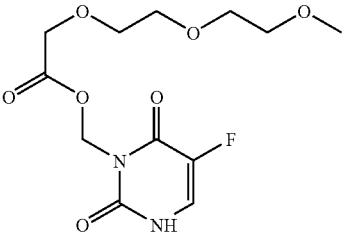 | 1.0 min | 437 min |
| 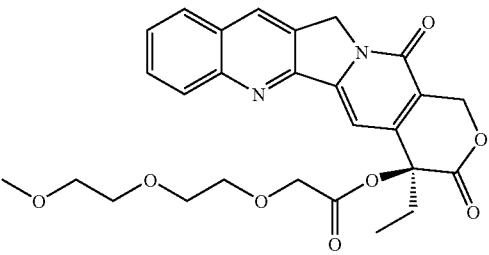 | 2 hr | 25 hr |

TABLE 1-continued
Half-lives of hydrolysis of the prodrugs in human serum and phosphate buffer at ph 7.4
| Structure | Serum | Buffer |
|---|---|---|
| 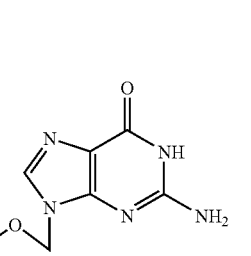 | 12 min | 26 hr |
| 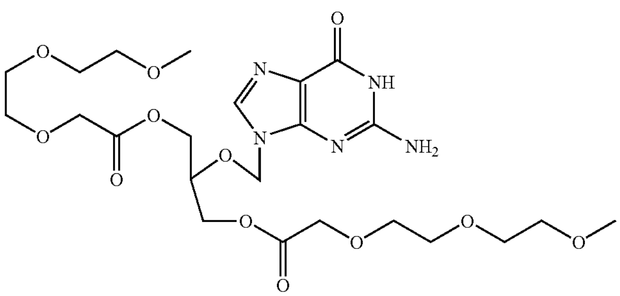 | 37 min | 10 hr |
| 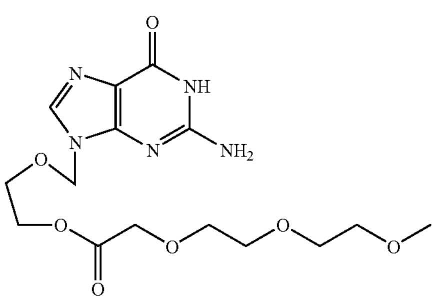 | 1 min | 22 hr |
| 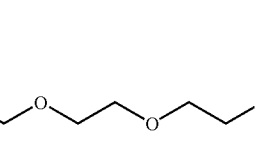 | stable | stable |

TABLE 1-continued
Half-lives of hydrolysis of the prodrugs in human serum and phosphate buffer at ph 7.4
| Structure | Serum | Buffer |
|---|---|---|
| 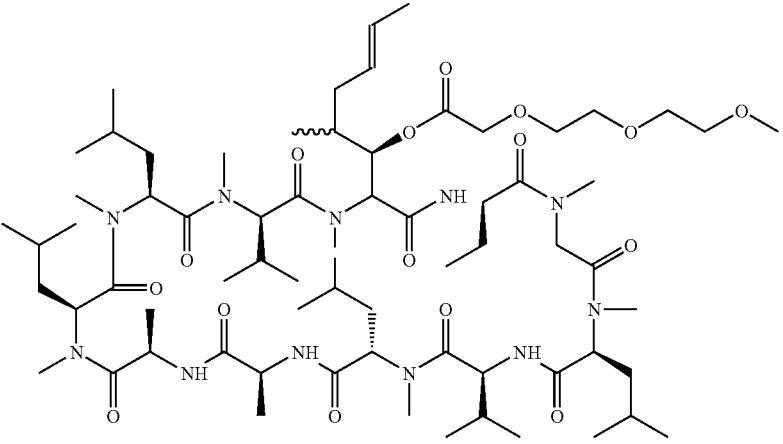 | stable | stable |
| 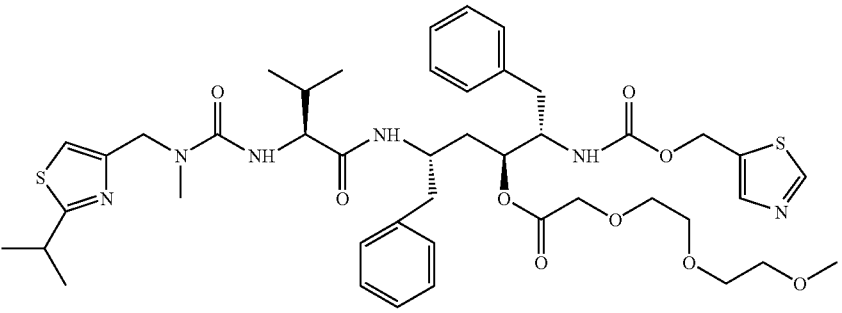 | >48 hr | >4 days |
| 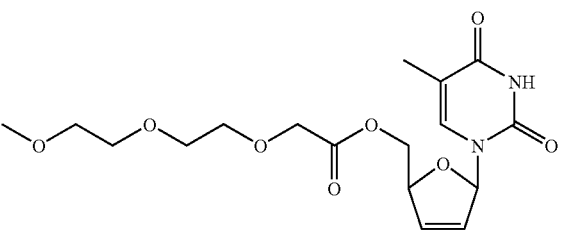 | | |
| 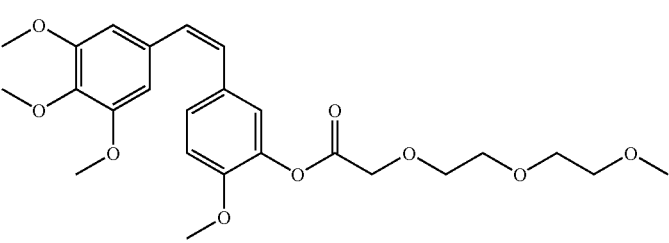 | 2 min | 10 hr |

TABLE 1-continued

Half-lives of hydrolysis of the prodrugs in human serum and phosphate buffer at ph 7.4

| Structure | Serum | Buffer |
|---|---|---|
| 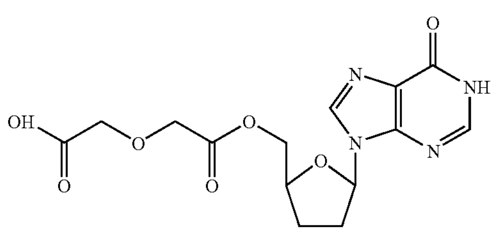 | 4.0 ± 0.5 min | 9.4 ± 0.1 hr |
| 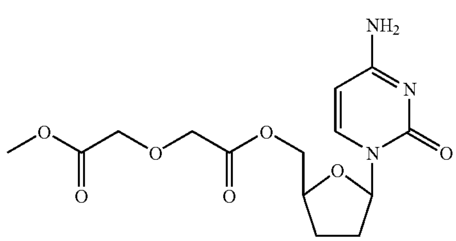 | 6.0 ± 0.2 min | 10.0 ± 0.5 hr |
| 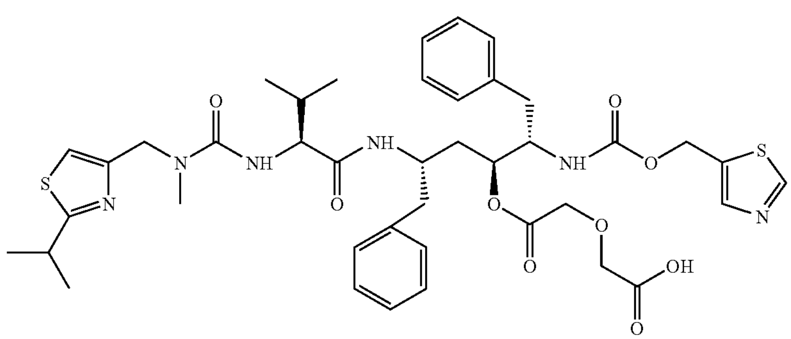 | 40 hr | >10 days |

TABLE 1-continued
Half-lives of hydrolysis of the prodrugs in human serum and phosphate buffer at ph 7.4
| Structure | Serum | Buffer |
|---|---|---|
| 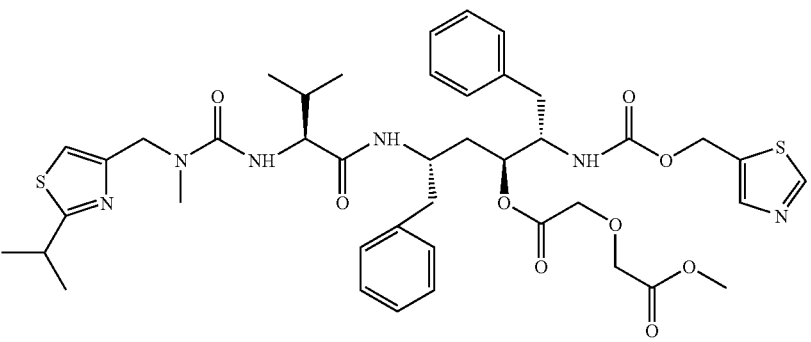 | 2.4 hr | 5.5 hr |
| 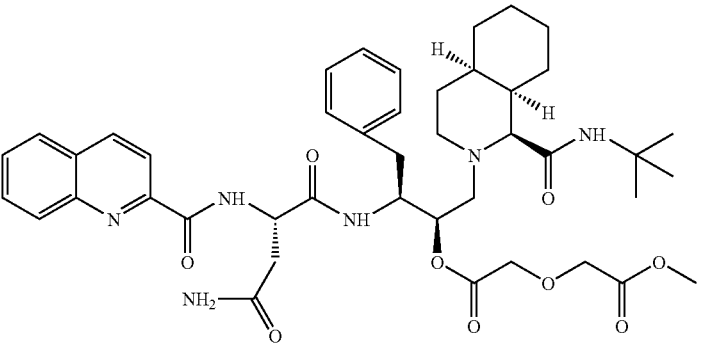 | 4.5 hr | 2.5 hr |
| 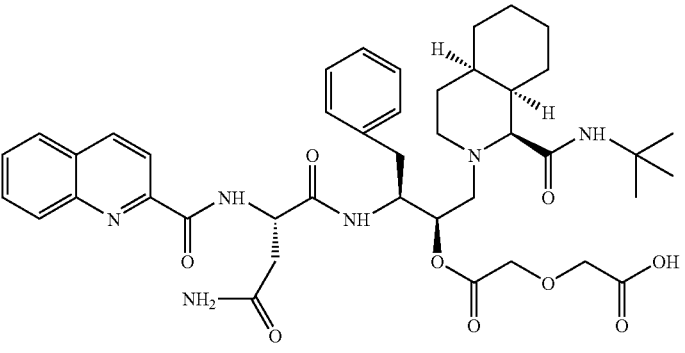 | | |
| 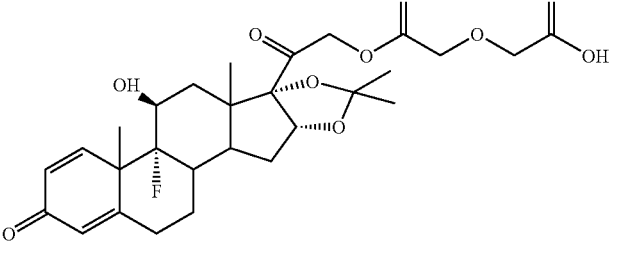 | 1 min | 1 hr |

TABLE 1-continued
Half-lives of hydrolysis of the prodrugs in human serum and phosphate buffer at ph 7.4
| Structure | Serum | Buffer |
|---|---|---|
| 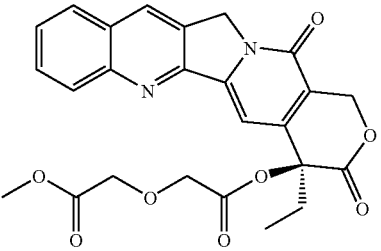 | 2 min | 6.1 hr |
| 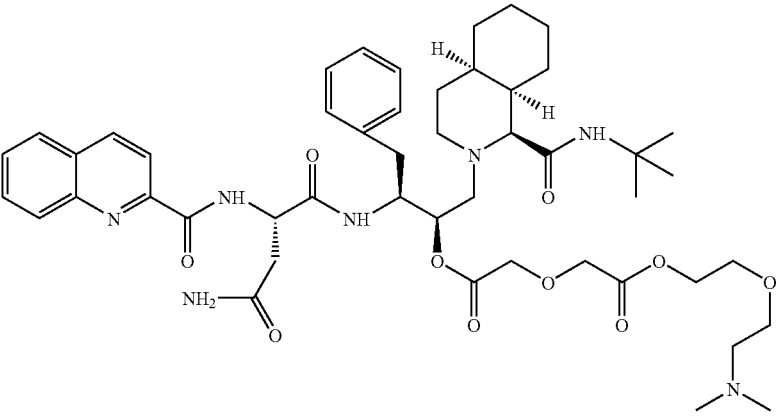 | 25 hr | 7 hr |
| 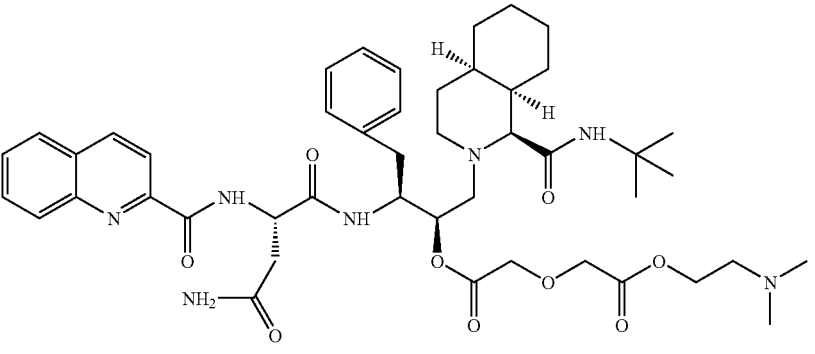 | 35 hr | 10 hr |
| 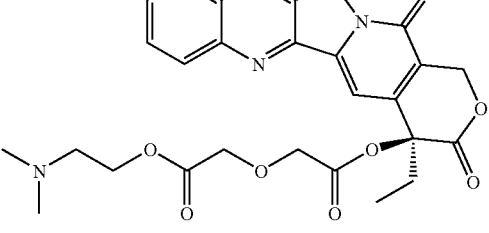 | <1 min | 5 min |
| 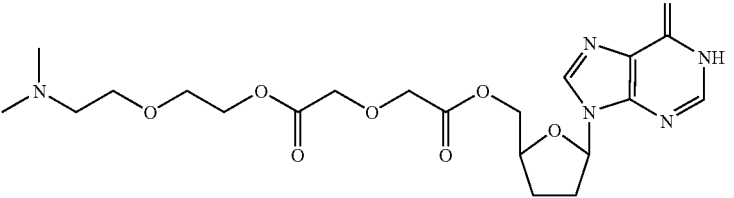 | 3 min | 3.5 hr |

TABLE 1-continued

Half-lives of hydrolysis of the prodrugs in human serum and phosphate buffer at ph 7.4

| Structure | Serum | Buffer |
|---|---|---|
| (cyclic peptide structure) | stable | stable |
| (camptothecin derivative structure) | 40 min | 3 hr |
| (peptidomimetic structure) | 1 hr | 2.2 hr |
| (steroid derivative structure) | | |

TABLE 1-continued
Half-lives of hydrolysis of the prodrugs in human serum and phosphate buffer at ph 7.4
| Structure | Serum | Buffer |
|---|---|---|
| 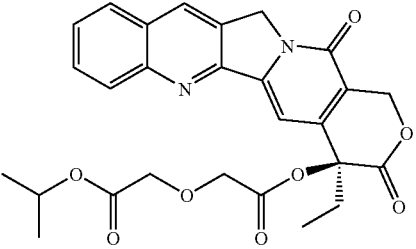 | | |
| 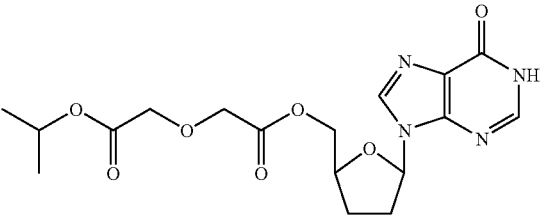 | 5 min<br>8 min | 10 hr<br>15 hr |
| 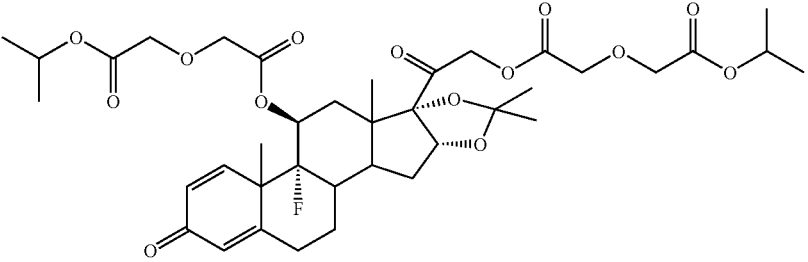 | | |
| 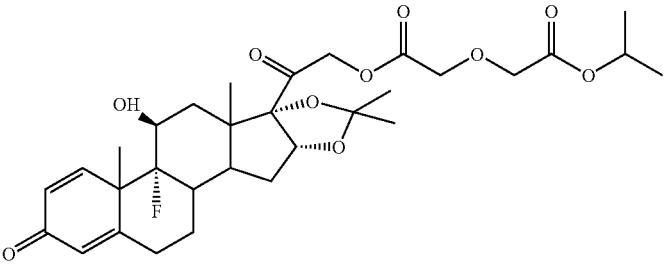 | | |
| 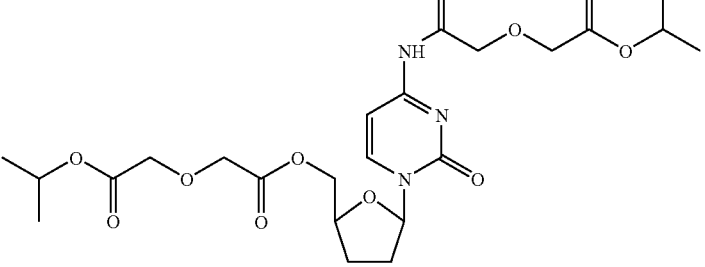 | 9.7 min | 5.6 hr |

TABLE 1-continued

Half-lives of hydrolysis of the prodrugs in human serum and phosphate buffer at ph 7.4

| Structure | Serum | Buffer |
|---|---|---|
| 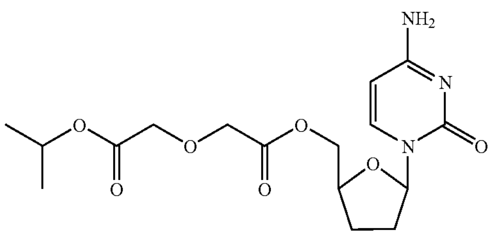 | 1.3 min | 8.2 hr |
| 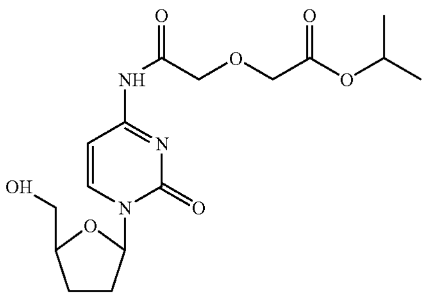 | 3.4 hr | 18 hr |
| 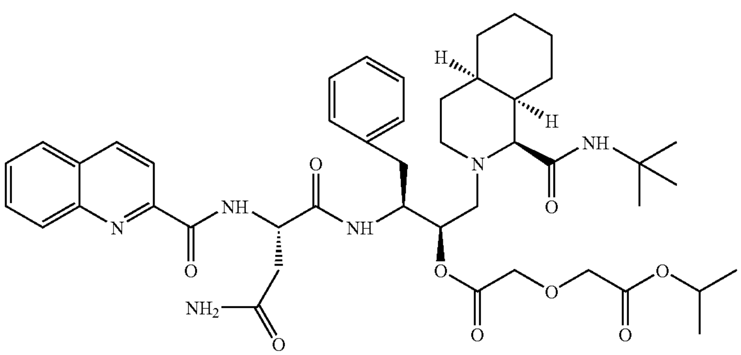 | 10 hr | 5 hr |
| | | |
| 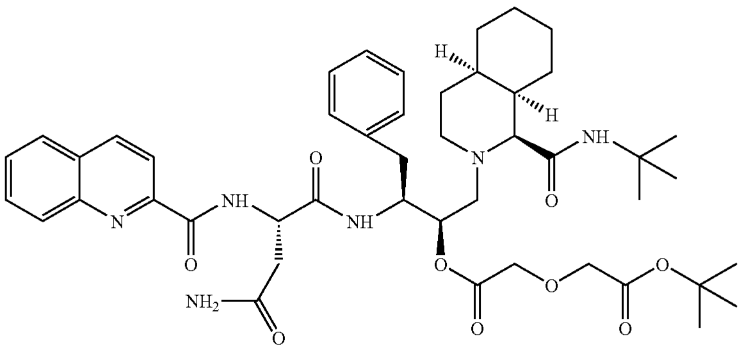 | 20 hr | 10 hr |

TABLE 1-continued

Half-lives of hydrolysis of the prodrugs in human serum and phosphate buffer at ph 7.4

| Structure | Serum | Buffer |
|---|---|---|
| 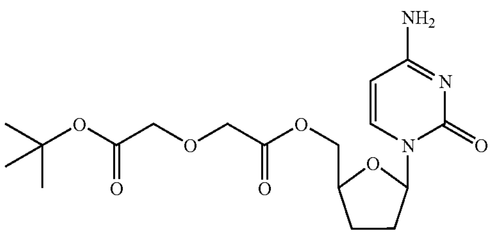 | 1.7 min | 11 hr |
| 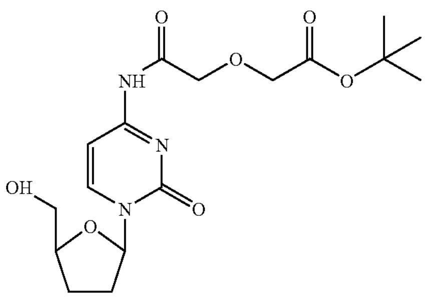 | 5 hr<br>6 hr; | 16 hr<br>20 hr; |
| 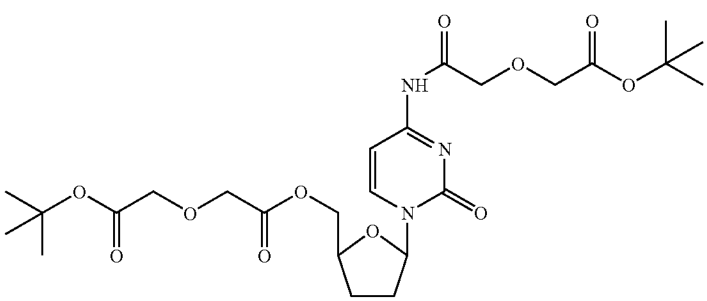 | 10.4 min | 6.2 hr |

TABLE 1-continued

Half-lives of hydrolysis of the prodrugs in human serum and phosphate buffer at ph 7.4

| Structure | Serum | Buffer |
|---|---|---|

TABLE 1-continued

Half-lives of hydrolysis of the prodrugs in human serum and phosphate buffer at ph 7.4

| Structure | Serum | Buffer |
|---|---|---|
| (structure) | 2.5 min | >2 days |
| (structure) | 2 min | 4 hr |
| (structure) | 7.4 min | 8.5 hr |
| (structure) | 25 hr | 40 hr |
| (structure) | 2.7 min | 16 hr |

TABLE 1-continued

Half-lives of hydrolysis of the prodrugs in human serum and phosphate buffer at ph 7.4

| Structure | Serum | Buffer |
|---|---|---|
| 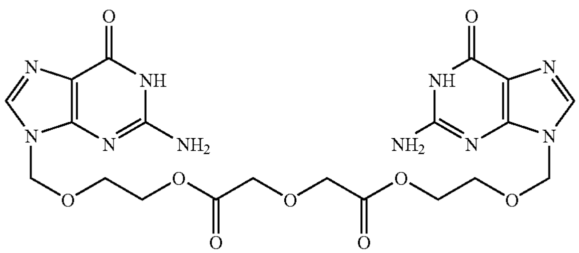 | 4 hr bis to mono | 10 hr bis to mono |
|  | 25 hr mono to drug | 40 hr mono to drug |

In the previous descriptions, numerous specific details are set forth, such as specific materials, structures, chemicals, processes, etc., in order to provide a better understanding of the present invention. However, the present invention can be practiced without resorting to the details specifically set forth. In other instances, well-known processing structures have not been described in detail in order not to unnecessarily obscure the present invention.

Only the preferred embodiment of the invention and but a few examples of its versatility are shown and described in the present disclosure. It is to be understood that the present invention is capable of use in various other combinations and environments and is capable of changes or modifications within the scope of the inventive concept as expressed herein. All patents, patent applications and publication cited herein are incorporated by reference in their entirety.

What is claimed is:

1. A prodrug having the following formula (I):

R-(DRUG) (I)

wherein the DRUG is a drug molecule covalently linked to R, and R is represented by the following formula (II):

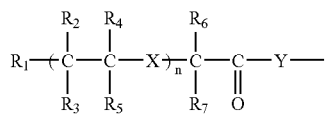
(II)

wherein

Y is selected from the group consisting of O, S and $NR^8$, where $R^8$ is selected from the group consisting of H or $C_1$–$C_4$ alkyl, $C_3$–$C_4$ branched alkyl and $C_3$–$C_4$ cycloalkyl;

X is O or S;

$R^1$ is selected from the group consisting of OH, $OR^9$, O—$CH_2$—COOH, $NH_2$ and $^+NH_3Z^-$ where $R^9$ is selected from the group consisting of $C_1$–$C_4$ alkyl, $C_3$–$C_4$ branched alkyl, and $C_3$–$C_4$ cycloalkyl and where $Z^-$ is a pharmaceutically acceptable salt anion;

$R^2$ is selected from the group consisting of H, $C_1$–$C_4$ alkyl, $C_1$–$C_4$ hydroxyalkyl;

$R^3$ is selected from the group consisting of H, $C_1$–$C_4$ alkyl, $C_1$–$C_4$ hydroxyalkyl;

$R^4$ is selected from the group consisting of H, $C_1$–$C_4$ alkyl, $C_1$–$C_4$ hydroxyalkyl;

$R^5$ is selected from the group consisting of H, $C_1$–$C_4$ alkyl, $C_1$–$C_4$ hydroxyalkyl;

$R^6$ is selected from the group consisting of H, $C_1$–$C_4$ alkyl, $C_1$–$C_4$ hydroxyalkyl;

$R^7$ is selected from the group consisting of H, $C_1$–$C_4$ alkyl, $C_1$–$C_4$ hydroxyalkyl; and n is a number from 1 to 12.

2. A pharmaceutical composition comprising the prodrug of claim 1 in an admixture of a pharmaceutically acceptable excipient or carrier or vehicle.

* * * * *